United States Patent [19]

Olsen et al.

[11] Patent Number: 5,525,716
[45] Date of Patent: Jun. 11, 1996

[54] LPT2 PROMOTER HAVING ALEURONE-TISSUE-SPECIFIC ACTIVITY

[76] Inventors: Odd-Arne Olsen, Tarnveien 16, 1430 As, Norway; Roger Kalla, Mowle Place, Weetangera A.C.T., 2614, Australia

[21] Appl. No.: 165,315

[22] Filed: Dec. 10, 1993

[30] Foreign Application Priority Data

Dec. 2, 1993 [GB] United Kingdom .................. 9324707

[51] Int. Cl.$^6$ .............................. C12N 15/00; C12N 5/04
[52] U.S. Cl. .................... 536/24.1; 435/172.3; 435/69.1; 435/91.4; 800/205; 536/24.3; 47/58
[58] Field of Search ................................ 536/274.1, 24.3; 800/205; 47/58; 435/172.3, 69.1, 94.1

[56] References Cited

FOREIGN PATENT DOCUMENTS

PCTWO90/01551 of 1990 WIPO.

OTHER PUBLICATIONS

Kalla et al. (1992) The promoter of the barley Ltp2 gene encoding an aleurone specific 7kDa lipid transfer protein contains a functional Myb binding site. EMBL/GenBank/DDBJ database.

[1]McElroy et al. (1990) Isolation of an Efficient Actin Promoter for use in Rice transformation, *The Plant Cell.* vol. 2, pp. 163–171.

Lewin, R. (1987) When does Homology mean something else? Science vol. 237. p. 1570. and Reeck et al. (1987) "Homology" in proteins and nucleic acids: A terminology muddle and a way out. Cell vol. 50, p. 667.

Reeck et al. (1987) "homology" in proteins and nucleic acids: A terminology middle and a way out of it. Cell. vol. 50. pp. 667.

Jakobsen et al. (1989) Barley aleurone cell development: molecular coling of aleurone specific cDNA's from immature grains. Plant Molecular Biology 12, pp. 285–293.

EMBL Database Ltp2 gene sequence.

Kalla, R., et al., (1993) Characterisation of promoter elements of aleurone specific genes from barley. In Pre–Harvest Sprouting in Cereals 1992. Eds. M. K. Walker–Simmons and J. J. Ried. The American Association of Cereal Chemists, Inc., ISBN 0-913250-81-3 pp. 236–245.

Olsen, O.-A., et al. (1990) Molecular Strategies for Improving Pre–Harvest Sprouting Resistance in Cereals. In Fifth International Symposium on Pre–Harvest Sprouting in Cereals, Westview Press, pp. 92–99.

*Primary Examiner*—Gary Benzion
*Attorney, Agent, or Firm*—St. Onge Steward Johnston & Reens

[57] ABSTRACT

The in vivo expression in the aleurone cells of a cereal of a conjugate is described. The conjugate comprises a GOI (gene of interest) and a particular Ltp (lipid transfer protein) promoter—namely the Ltp2 gene promoter. The conjugate is stably integrated within the cereal's genomic DNA.

14 Claims, 8 Drawing Sheets

FIGURE 1

```
-807                              GATCTCGATGTGTAGTCTACGAGAAGG
-780  GTTAACCGTCTCTTCGTGAGAATAACCGTGGCCTAAAAATAAGCCGATGAGGATAAATAA
-720  AATGTGGTGGTACAGTACTTCAAGAGGTTTACTCATCAAGAGGATGCTTTTCCGATGAGC
-660  TCTAGTAGTACATCGGACCTCACATACCTCCATTGTGGTGAAATATTTTGTGCTCATTTA
-600  GTGATGGGTAAATTTTGTTTATGTCACTCTAGGTTTTGACATTTCAGTTTTGCCACTCTT
-540  AGGTTTTGACAAATAATTTCCATTCCGCGGCAAAAGCAAAACAATTTTATTTTACTTTTA
-480  CCACTCTTAGCTTTCACAATGTATCACAAATGCCACTCTAGAAATTCTGTTTATGCCACA
-420  GAATGTGAAAAAAAACACTCACTTATTTGAAGCCAAGGTGTTCATGGCATGGAAATGTGA
-360  CATAAAGTAACGTTCGTGTATAAGAAAAAATTGTACTCCTCGTAACAAGAGACGGAAACA
-300  TCATGAGACAATCGCGTTTGGAAGGCTTTGCATCACCTTTGGATGATGCGCATGAATGGA
-240  GTCGTCTGCTTGCTAGCCTTCGCCTACCGCCCACTGAGTCCGGGCGG***CAACTA***CCATCGG
-180  CGAACGACC***CAGCTG***ACCTCTACCGACCGGACTTGAATGCGCTACCTTCGTCAGCGACGA
-120  TGGCCGCGTACGCTGGCGACGTGCCCCCG***CATGCATG***GCGGCACATGGCGAGCTCAGACC
- 60  GTGCGTGGCTGGC[TACAAA]TACGTACCCCGTGAGTGCCCTAGCTAGAAACTTACACCTGC
   1    AACTGCGAGAGCGAGCGTGTGAGTGTAGCCGAGTAGATCACCGTACGACGACGACGAGG
  60  GGCATGGCGATGGCGATGGGGATGGCGATGAGGAAGGAGGCAGCGGTGGCCGTGATGATG
 120  GTGATGGTGGTGACGCTGGCGGCGGGTGCGGACGCGGGAGCGGGAGCGGCGTGCGAGCCG
 180  GCGCAGCTGGCGGTGTGCGCGTCGGCGATCCTGGGCGGGACGAAGCCGAGCGGCGAGTGC
 240  TGCGGGAACCTGCGGGCGCAGCAGGGGTGCTTGTGCCAGTACGTCAAGGACCCCAACTAC
 300  GGGCACTACGTGAGCAGCCCACACGCGCGCGACACCCTCAACTTGTGCGGCATACCCGTA
 360  CCGCACTGCTAGCCGCCTAGCCGATCGAGGGCTCCAGGCACGCATGCATGTTCCTGTTAT
 420  GTGTATGTTGGAATAAAATGCTGGTGATCTATGGCGGCTAGCTTGCTTCCTGGCTAGCAG
 480  CTGCTGTAATGAAATTTGTGTTGCAACTTTTTTTTTAGTCC
```

FIGURE 2A

```
-807                                           GATCTCGATGTGTAGTCTACGAGAAGG
-780   GTTAACCGTCTCTTCGTGAGAATAACCGTGGCCTAAAAATAAGCCGATGAGGATAAATAA
-720   AATGTGGTGGTACAGTACTTCAAGAGGTTTACTCATCAAGAGGATGCTTTTCCGATGAGC
-660   TCTAGTAGTACATCGGACCTCACATACCTCCATTGTGGTGAAATATTTTGTGCTCATTTA
-600   GTGATGGGTAAATTTTGTTTATGTCACTCTAGGTTTTGACATTTCAGTTTTGCCACTCTT
-540   AGGTTTTGACAAATAATTTCCATTCCGCGGCAAAAGCAAAACAATTTTATTTTACTTTTA
-480   CCACTCTTAGCTTTCACAATGTATCACAAATGCCACTCTAGAAATTCTGTTTATGCCACA
-420   GAATGTGAAAAAAAACACTCACTTATTTGAAGCCAAGGTGTTCATGGCATGGAAATGTGA
-360   CATAAAGTAACGTTCGTGTATAAGAAAAAATTGTACTCCTCGTAACAAGAGACGGAAACA
-300   TCATGAGACAATCGCGTTTGGAAGGCTTTGCATCACCTTTGGATGATGCGCATGAATGGA
-240   GTCGTCTGCTTGCTAGCCTTCGCCTACCGCCCACTGAGTCCGGGCGGCAACTACCATCGG
-180   CGAACGACCCAGCTGACCTCTACCGACCGGACTTGAATGCGCTACCTTCGTCAGCGACGA
-120   TGGCCGCGTACGCTGGCGACGTGCCCCCGCATGCATGGCGGCACATGGCGAGCTCAGACC
-060   GTGCGTGGCTGGC[TACAAA]TACGTACCCCGTGAGTGCCCTAGCTAGAAACTTACACCTGC
```

FIGURE 2B

```
-807                              GATCTCGATGTGTAGTCTACGAGAAGG
-780    GTTAACCGTCTCTTCGTGAGAATAACCGTGGCCTAAAAATAAGCCGATGAGGATAAATAA
-720    AATGTGGTGGTACAGTACTTCAAGAGGTTTACTCATCAAGAGGATGCTTTTCCGATGAGC
-660    TCTAGTAGTACATCGGACCTCACATACCTCCATTGTGGTGAAATATTTTGTGCTCATTTA
-600    GTGATGGGTAAATTTTGTTTATGTCACTCTAGGTTTTGACATTTCAGTTTTGCCACTCTT
-540    AGGTTTTGACAAATAATTTCCATTCCGCGGCAAAAGCAAAACAATTTTATTTTACTTTTA
-480    CCACTCTTAGCTTTCACAATGTATCACAAATGCCACTCTAGAAATTCTGTTTATGCCACA
-420    GAATGTGAAAAAAAACACTCACTTATTTGAAGCCAAGGTGTTCATGGCATGGAAATGTGA
-360    CATAAAGTAACGTTCGTGTATAAGAAAAAATTGTACTCCTCGTAACAAGAGACGGAAACA
-300    TCATGAGACAATCGCGTTTGGAAGGCTTTGCATCACCTTTGGATGATGCGCATGAATGGA
-240    GTCGTCTGCTTGCTAGCCTTCGCCTACCGCCCACTGAGTCCGGGCGGCAACTACCATCGG
-180    CGAACGACCCAGCTGACCTCTACCGACCGGACTTGAATGCGCTACCTTCGTCAGCGACGA
-120    TGGCCGCGTACGCTGGCGACGTGCCCCCGCATGCATGGCGGCACATGGCGAGCTCAGACC
- 60    GTGCGTGGCTGGC[TACAAA]TACGTACCCCGTGAGTGCCCTAGCTAGAAACTTACACCTGC
   1    AACTGCGAGAGCGAGCGTGTGAGTGTAGCCGAGTAGATC
```

FIGURE 7

```
        MYB                  MYC
       TAACTG               CANNTG
        C  G
Lto2 GGCAACTACCATCGGCGAACGACCCAGCTGACCTCTACCGACCGGACTTG- 98nt-TACAAA
```

LPT2 PROMOTER HAVING ALEURONE-TISSUE-SPECIFIC ACTIVITY

The present invention relates to a promoter and to a conjugate comprising the same. The present invention also relates to the use of the promoter for stage- and tissue-specific expression of a gene of interest (GOI). The present invention also relates to the genomic nucleotide sequence of, and isolation of, the promoter.

In particular the present invention relates to a promoter for a lipid transfer protein (Ltp) gene known as the Ltp2 gene. The present invention also relates to the application of this Ltp2 gene promoter to express a GOI specifically in the aleurone layer of a monocotyledon-especially a transgenic cereal seed—more especially a developing transgenic cereal seed.

A mature cereal seed contains two distinct organs: the embryo—which gives rise to the vegetative plant—and the endosperm—which supports the growth of the emerging seedling during a short period of time after germination. The endosperm, which is the site of deposition of different storage products such as starch and proteins, is further sub-divisible into a peripheral layer of living aleurone cells surrounding a central mass of non-living starchy endosperm cells.

The aleurone cells differentiate from primary endosperm cells early during seed development or between 10 to 21 days after fertilization. The aleurone layer and embryo share many similarities in their gene expression programmes. They are the only cereal seed tissues that survive the desiccation process during seed maturation and they both have active gene transcription during seed germination.

The aleurone layer of cereal seeds comprises specialized cells that surround the central starchy endosperm, i.e. the site for starch and protein accumulation in the developing seed (Bosnes et al., 1992, Olsen et al., 1992). During seed germination, the cells of the aleurone layer produce amylolytic and proteolytic enzymes that degrade the storage compounds into metabolites that are taken up and are used by the growing embryo. Two aspects of aleurone cell biology that have been intensively studied are the genetics of anthocyanin pigmentation of aleurone cells in maize (McClintock, 1987) and the hormonal regulation of gene transcription in the aleurone layer of germinating barley seeds (Fincher, 1989).

Using transposon tagging, several structural and regulatory genes in the anthocyanin synthesis pathway have been isolated and characterized (Paz-Ares et at., 1987; Dellaporta et al., 1988). In barley, alpha-amylase and beta-glucanase genes that are expressed both in the aleurone layer and embryos of mature germinating seeds have been identified (Karrer et al., 1991; Slakeski and Fincher, 1992). In addition, two other cDNAs representing transcripts that are differentially expressed in the aleurone layers of developing barley grains have been isolated. These are CHI26 (Lea et al.,1991) and pZE40 (Smith et al., 1992). For none of these gene products has it been shown in transgenic cereal plants that the promoter directs expression in just the aleurone layer of developing grains.

Non-specific lipid transfer proteins (nsLtp's) have the ability to mediate in vitro transfer of radiolabelled phospholipids from liposomal donor membranes to mitochondrial acceptor membranes (Kader et al., 1984; Watanabe and Yamada, 1986). Although their in vivo function remains unclear, nsLTPs from plants have recently received much attention due to their recurrent isolation as cDNA clones representing developmentally regulated transcripts expressed in several different tissues. A common feature is that, at some point in development, they are highly expressed in tissues producing an extracellular layer rich in lipids. Thus, transcripts corresponding to cDNAs encoding 10 kDa nsLTPs have been characterized in the tapetum cells of anthers as well as the epidermal layers of leafs and shoots in tobacco (Koltunow et al., 1990; Fleming et al., 1992), and barley aleurone layers (Mundy and Rogers, 1986; Jakobsen et al., 1989).

In addition, a 10 kDa nsLTP was discovered to be one of the proteins secreted from auxintreated somatic carrot embryos into the tissue culture medium (Sterk et al., 1991). Based on in situ data demonstrating that the Ltp transcripts are localized in the protoderm cells of the somatic and zygotic carrot embryo and in the epithelial layer of the maize embryonic scutellum, it was suggested that in vivo nsLTPs are involved in either cutin biosynthesis or in the biogenesis and degradation of storage lipids (Sossountzov et al., 1991; Sterk et al., 1991).

A nsLTP in Arabidopsis has been localized to the cell walls lending further support to an extracellular function if this class of proteins (Thoma et al., 1993). PCT WO 90/01551 mentions the use of the aleurone cells of mature, germinating seeds to produce proteins from GOIs under the control of an alpha-amylase promoter. This promoter is active only in germinating seeds.

Recently, using a standard in vitro Ltp assay, two 10 kDa and one member of a novel class of 7 kDa nsLtp's were isolated from wheat seeds (Monnet, 1990; Dieryck et al., 1992). The sequence of this 7 kDa wheat nsLtp protein shows a high degree of similarity with the predicted protein from the open reading frame (ORF) of the Bz11E cDNA, which had been isolated in a differential screening for barley aleurone specific transcripts (Jakobsen et al., 1989). However, the amino acid sequence of this polypeptide showed only limited sequence identities with the previously sequenced 10 kDa proteins. In sub-cellular localisation studies using gold labelled antibodies one 10 kDa protein from Arabidopsis was localised to the cell wall of epidermal leaf cells. The presence of a signal peptide domain in the N-terminus of the open reading frames of all characterised plant ns-LTP cDNAs, also suggests that these are proteins destined for the secretory pathway with a possible extracellular function.

Olsen et al. in a paper titled "Molecular Strategies For Improving Pre-Harvest Sprouting Resistance In Cereals" published in 1990 in the published extracts from the Fifth International Symposium On Pre-Harvest Sprouting In Cereals (Westview Press Inc.) describe three different strategies for expressing different "effector" genes in the aleurone layer and the scutellum in developing grains of transgenic plants. This document mentions 4 promoter systems—including a system called B11E (which is now recognised as being the same as the Ltp2 gene promoter). There is no sequence listing for B11E given in this document.

Kalla et al. (1993) in a paper titled "Characterisation of Promoter Elements Of Aleurone Specific Genes From Barley" describe the possibility of the expression of anti-sense genes by the use of promoters of the aleurone genes B22E, B23D, B14D, and B11E (which is now shown to be the same as Ltp2).

The Kalla et al. (1993) paper gives a very general map of the Ltp2 gene promoter. The transient expression results showed very low levels of expression of the reporter gene.

A sequence listing of the Ltp2 gene was available as of 23 Dec. 1992 on the EMBL database.

One of the major limitations to the molecular breeding of new varieties of crop plants with aleurone cells expressing GOIs is the lack of a suitable aleurone specific promoter.

At present, the available promoters—such as the CaMV 35S, rice actin and maize alcohol dehydrogenase—all are constitutive. In this regard, they are non-specific in target site or stage development as they drive expression in most cell types in the plants.

Another problem is how to achieve expression of a product coded for by a GOI in the aleurone layer of the endosperm that gives minimal interference with the developing embryo and seedling.

It is therefore desirable to provide aleurone specific expression of GOIs in cereal such as rice, maize, wheat, barley and other transgenic cereal plants.

Moreover it is desirable to provide aleurone specific expression that does not lead to the detriment of the developing embryo and seedling.

According to a first aspect of the present invention there is provided a Ltp2 gene promoter comprising:

the sequence shown as SEQ. I.D. 1, or a sequence that has substantial homology with that of SEQ. I.D. 1, or a variant thereof.

According to a second aspect of the present invention there is provided a conjugate comprising a GOI and a Ltp2 gene promoter as just defined.

According to a third aspect of the present invention there is provided an in vivo expression system comprising a conjugate comprising a GOI and a Ltp2 gene promoter as just defined wherein the conjugate is integrated, preferably stably integrated, within a monocotyledon's (preferably a cereal's) genomic DNA.

According to a fourth aspect of the present invention there is provided a transgenic cereal comprising a conjugate comprising a GOI and a Ltp2 gene promoter as just defined wherein the conjugate is integrated, preferably stably integrated, within a cereal's genomic DNA.

According to a fifth aspect of the present invention there is provided the in vivo expression in the aleurone cells of a monocotyledon (preferably a cereal) of a conjugate comprising a GOI and a Ltp2 gene promoter as just defined; wherein the conjugate is integrated, preferably stably integrated, within the monocotyledon's genomic DNA.

According to a sixth aspect of the present invention there is provided a method of enhancing the in vivo expression of a GOI in just the aleurone cells of a monocotyledon (preferably a cereal) which comprises stably inserting into the genome of those cells a DNA conjugate comprising a Ltp2 gene promoter as just defined and a GOI; wherein in the formation of the conjugate the Ltp2 gene promoter is ligated to the GOI in such a manner that each of the myb site and the myc site in the Ltp2 gene promoter is maintained substantially intact.

According to a seventh aspect of the present invention there is provided the use of a myb site and a myc site in an Ltp2 gene promoter to enhance in vivo expression of a GOI in just in the aleurone cells of a monocotyledon (preferably a cereal) wherein the Lip2 gene promoter and the GOI are integrated into the genome of the monocotyledon.

According to an eighth aspect of the present invention there is provided a method of enhancing the in vivo expression of a GOI in just the aleurone cells of a monocotyledon (preferably a cereal) which comprises stably inserting into the genome of those cells a DNA conjugate comprising a Ltp2 gene promoter as just defined and a GOI; wherein in the formation of the conjugate the Ltp2 gene promoter is ligated to the GOI in such a manner that any one of the Sphl site, the AL site or the DS site in the Ltp2 gene promoter is (are) maintained substantially intact. The Sphl site, the AL site and the DS site are defined later.

Preferably the promoter is a barley aleurone specific promoter.

Preferably the promoter is for a 7 kDa lipid transfer protein.

Preferably the promoter is used for expression of a GOI in a cereal seed.

Preferably the promoter is used for expression of a GOI in a monocotyledonous species, including a grass—preferably a transgenic cereal seed.

Preferably the cereal seed is anyone of a rice, maize, wheat, or barley seed.

Preferably the promoter is the promoter for Ltp2 of *Hordeum vulgare*.

Preferably at least one additional sequence is attached to the promoter gene or is present in the conjugate to increase expression of a GOI or the GOI.

The additional sequence may be one or more repeats (e.g. tandem repeats) of the promoter upstream box(es) which are responsible for the aleurone specific pattern of expression of Ltp2. The additional sequence may even be a Sh1-intron.

The term "GOI" with reference to the present invention means any gene of interest—but not the remainder of the natural Ltp2 gene for the cereal in question. A GOI can be any gene that is either foreign or natural to the cereal in question.

Typical examples of a GOI include genes encoding for proteins giving for example added nutritional value to the seed as a food or crop or for example increasing pathogen resistance. The GOI may even be an antisense construct for modifying the expression of natural transcripts present in the relevant tissues.

Preferably the GOI is a gene encoding for any one of a protein having a high nutritional value, a *Bacillus thuringensis* insect toxin, or an alpha- or beta- amylase or germination induced protease antisense transcript.

The term "a variant thereof" with reference to the present invention means any substitution of, variation of, modification of, replacement of, deletion of or the addition of one or more nucleic acid(s) from or to the listed promoter sequence providing the resultant sequence exhibits aleurone specific expression.

The term "substantial homology" covers homology with respect to at least the essential nucleic acids of the listed promoter sequence providing the homologous sequence exhibits aleurone specific expression. Preferably there is at least 80% homology, more preferably at least 90% homology, and even more preferably there is at least 95 % homology with the listed promoter sequence.

The term "maintained substantially intact" means that at least the essential components of each of the myb site and the myc site remain in the conjugate to ensure aleurone specific expression of a GOI. Preferably at least about 75%, more preferably at least about 90%, of the myb or myc site is left intact.

The term "conjugate", which is synonymous with the terms "construct" and "hybrid", covers a GOI directly or indirectly attached to the promoter gene to from a Ltp2-GOI cassette. An example of an indirect attachment is the provision of a suitable spacer group such as an intron sequence, such as the Sh1-intron, intermediate the promoter and the GOI.

The present invention therefore provides the novel and inventive use of an aleurone specific promoter—namely the use of the Ltp2 gene promoter, preferably the Ltp2 gene promoter from barley.

The main advantage of the present invention is that the use of the Ltp2 gene promoter results in specific aleurone expression of a GOI in the aleurone layer(s) of cereals such as rice, maize, wheat, barley and other transgenic cereal seeds, preferably maize seed.

It is particularly advantageous that the expression is both stage- and tissue- specific.

A further advantage is that the expression of the product coded for by a GOI in the aleurone layer of the endosperm gives minimal interference with the developing embryo and seedling. This is in direct contrast to constitutive promoters which give high levels of expression in the developing seedling and mature plant tissues which severely affect normal plant development.

The present invention is particularly useful for expressing GOI in the aleurone layer of developing grains—such as cereal seeds.

With regard to the present invention it is to be noted the EMBL database sequence listing (ibid) does not suggest that the Ltp2 gene promoter could be used to express a GOI in a stage- and tissue- specific manner. Also the database extract does not mention the importance of the myb gene segment or the myc gene segment.

It is also to be noted the paper titled "Molecular Strategies For Improving Pre-Harvest Sprouting Resistance In Cereals" (ibid) does not give any specific sequence listing information for the Ltp2 gene promoter. Also there is no explicit mention in this paper of using just the Ltp2 gene promoter to induce expression in just aleurone cells. Moreover, there is no mention in this paper of an Ltp2—GOI conjugate being formed. Also there is no mention in this paper of the importance of the myb site or the myc site.

It is also to be noted that in the paper titled "Characterisation of Promoter Elements Of Aleurone Specific Genes From Barley" (ibid) there is no mention of an Ltp2—GOI conjugate stably integrated into genomic DNA of a cereal. Also there is no explicit disclosure of an in vivo expression system. Moreover, there is no full sequence listing in this paper for the Ltp2 gene promoter. Also there is no explicit mention in this paper of the importance of the myb site or the myc site of Ltp2 gene promoter for in vivo GOI expression.

In contrast to the work disclosed in PCT WO 90/01551, the Ltp2 gene promoter (which is not disclosed in PCT WO 90/01551) the Ltp2 gene promoter results in aleurone specific expression in developing grains.

In general, therefore, the present invention relates to a promoter for a Ltp2 gene encoding a 7 kDa nsLTP. In situ hybridization analysis demonstrates that the Ltp2 transcript is expressed exclusively in aleurone cells from the beginning of the differentiation stage and half-way into the maturation stage. Further commentary on the maturation stages is provided by Bosnes et al., 1992.

The Ltp2 gene promoter may be inserted into a plasmid. For example, the Ltp2 BglII 0.84 kb fragment can be inserted into the BamHI site of Bluescript. A GOI, such as GUS, can then be inserted into this conjugate (construct). Furthermore, a Sh1 intron can then be inserted into the SmaI site of this conjugate.

Stable integration may be achieved by using the method of Shimamoto (1989). Another way is by bombardment of an embryonic suspension of cells (e.g. maize cells). Another way is by bombardment of immature embryos (e.g. barley embryos).

With the present invention, it can be shown by using particle bombardments that the −807 bp Ltp2 gene promoter fused to a beta-glucuronidase (GUS) reporter gene (which serves as a GOI) is active in the aleurone layer of developing barley seeds, giving 5% of the activity of the strong constitutive actin-promoter from rice. Also, in transgenic rice plants, the barley Ltp2-promoter directs strong expression of the GUS-reporter gene exclusively in the aleurone layer of developing seeds, suggesting the presence of conserved mechanisms for aleurone cell gene expression in the cereals.

In a preferred embodiment, the Ltp2 gene encodes a 7 kDa barley seed nsLTP and has about 80% identity to the wheat 7 kDa protein.

The transcript of the Ltp2 gene is detectable in the earliest morphologically distinguishable aleurone cells and accumulates during the differentiation stage to decline finally during seed maturation. It can also serve as a molecular marker for the differentiating aleurone cells as shown in situ hybridisation experiments where the spatial distribution of the transcript is to be examined.

In the present invention, a genomic clone was isolated using the cDNA insert of previously isolated cDNA clone pBz 11E and characterised by DNA sequencing.

The sequence of the cDNA and isolated genomic clone was found to be identical in the overlapping region. It was found the Ltp2 gene does not contain any intron.

To prove that this is an active gene, the 5' region carried on a 845 bp DNA fragment delineated by two Bgl II restriction sites was fused to the GUS gene (following Jefferson 1987) and the construct was introduced into barley aleurone layers using micro projectile bombardment. Aleurone cells expressing GUS activity were detected proving that the gene promoter was indeed capable of driving the expression of the GOI in the relevant tissue.

By comparing the DNA sequence of this active promoter sequences several putative cis-acting elements with the potential of binding known transcriptional factors present in cereal aleurone layers were detected. They include the binding sites for transcriptional factors of the myb and myc class, namely TAACTG and CANNTG respectively. Our experiments showed that the myb and myc sites were important for good levels of expression.

Gel retardation experiments showed that the Ltp2 gene promoter has a myb site that is recognised by a MYB protein (e.g. from chicken).

In the present invention, mature fertile rice plants were regenerated from transformed cultured rice protoplasts. The developing seeds of these primary transformants were analysed for the expression of GUS. It was found that the barley seed Ltp2 gene promoter confers aleurone specific expression in transgenic rice plants. This is the first example of an aleurone specific promoter in developing seeds of a transgenic cereal.

The following were deposited in accordance with the Budapest Treaty at the recognised depositary The National Collections of Industrial and Marine Bacteria Limited (NCIMB) at 23 St Machar Drive, Aberdeen, Scotland, UK, AB2 1RY, on 22 Nov. 1993:

(i) An *E. Coli* K12 bacterial stock containing the plasmid pLtp2pr—i.e. Bluescript containing the Ltp2 gene promoter (Deposit Number NCIMB 40598).

(To form pLtp2pr, the Ltp2 promoter of FIG. 2b (see later) contained on a BglII fragment was inserted in the Bluescript KS vector into the BamHI site.)

(ii) An *E. Coli* K12 bacterial stock containing the plasmid pLtp2/GN—i.e. Bluescript containing a Ltp2 gene promoter—GUS conjugate (Deposit Number NCIMB 40599).

(To form pLtp2/GN, the GUS-reporter gene cassette (GN) contained on the SmaI-EcoRI fragment of the commercially available vector pBI101 (Clontech Inc.) was cloned directionally into the SmaI and EcoRI sites of pLtp2pr.)

(iii) An *E. Coli* K12 bacterial stock containing the plasmid pLtp2, ΔBCIGN—i.e. Bluescript containing an Ltp2 gene promoter with a deletion spanning the myb and myc sites—GUS conjugate (Deposit Number NCIMB 40601).

(To form pLtp2ΔBCIGN, the Ltp2 promoter and the GN gene was inserted as described for pLtp2pr and pLtp2/GN except for the use of Bluescript SK and that the Ltp2 promoter was deleted in the myb-myc region (using a PCR strategy) as explained in the legend of FIG. 7 (see later).)

(iv) An *E. Coli* K12 bacterial stock containing the plasmid pLtp2Sh1/GN—i.e. Bluescript containing an Ltp2 gene promoter-Sh1 intron-GUS conjugate (Deposit No. NCIMB 40600).

(To form pLtp2sh1/GN, the Ltp2 promoter and the GN gene was inserted as described for pLtp2pr and pLtp2/GN except for the use of Bluescript SK. The Sh1 intron from maize contained on a Hincll restriction fragment was inserted into the Sma1 site of this construct.)

Other embodiments and aspects of the present invention include: A transformed host having the capability of expressing a GOI in just the aleurone layer; A vector incorporating a conjugate as hereinbefore described or any part thereof; A plasmid comprising a conjugate as hereinbefore described or any part thereof; A cellular organism or cell line transformed with such a vector; A monocotylenedonous plant comprising any one of the same; A developing seed comprising any of the same; and A method of expressing any one of the same.

The file of this patent contains at least one drawing executed in color. Copies of this patent with color drawings will be provided by the Patent and Trademark Office upon request and payment of the necessary fee.

BRIEF DESCRIPTION OF THE FIGURES

The present invention will now be described only by way of examples in which reference shall be made to the accompanying Figures in which:

FIG. 1 is a nucleotide sequence of the Ltp2 gene (SEQ ID No. 3);

FIG. 2*a* is a nucleotide sequence of the Ltp2 gene promoter;

FIG. 2*b* is a nucleotide sequence of the Ltp2 gene promoter (SEQ ID No. 1) with an additional 39 nucleotides for fusion to a GUS gene for transgenic rice and transient assay studies (SEQ ID No. 2);

FIG. 7 shows the position of the myb and myc binding sites in the barley Ltp2 gene promoter.

A. METHODS i. Plant material

Figure 3:
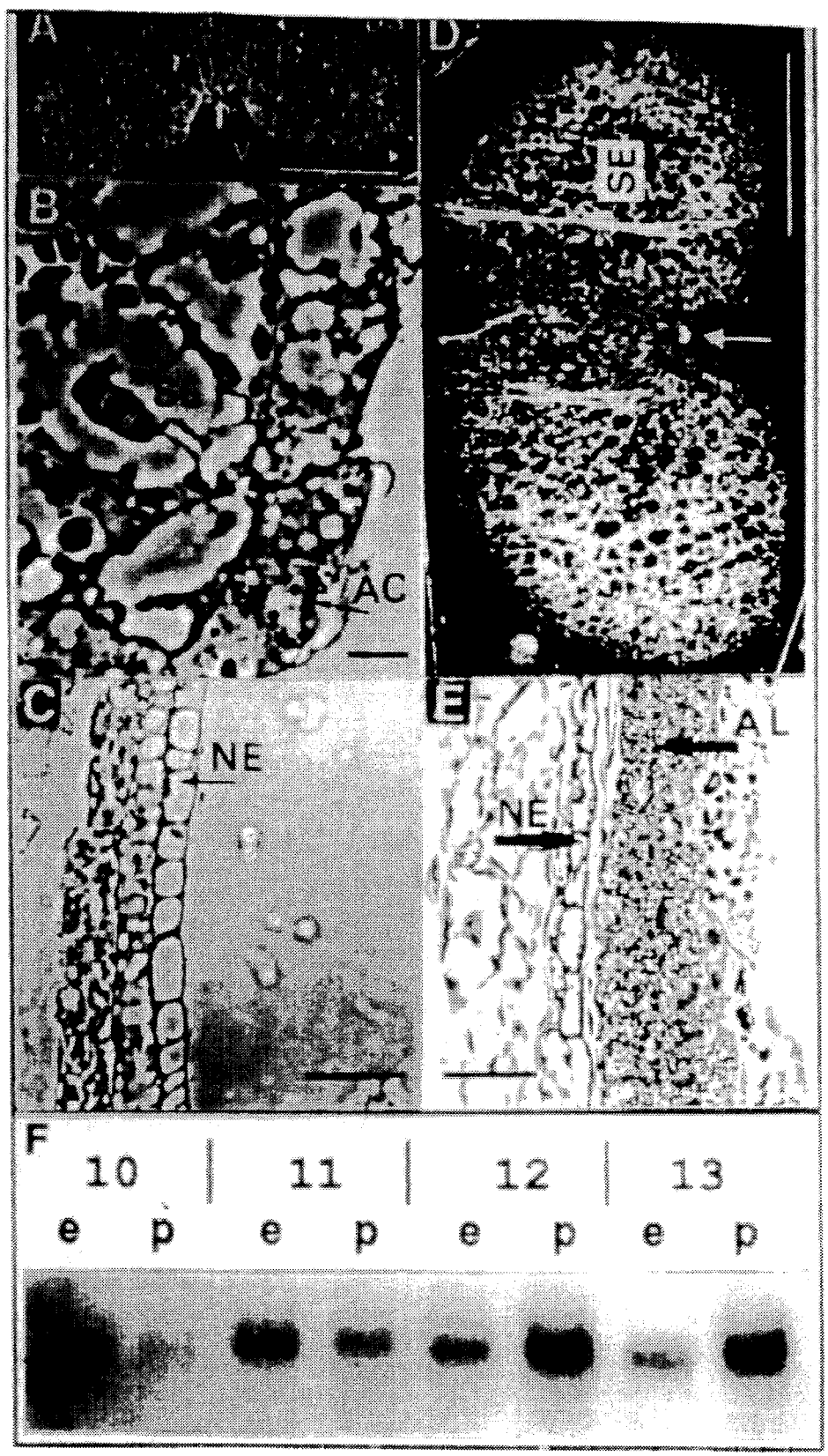
FIG. 3 shows transverse sections from the mid-region of barley seeds (A-E) and steady state levels of the Ltp2 mRNA in different tissue fractions of developing barley endosperm.

Seeds of Barley (*Hordeum vulgare* cv. Bomi) were collected from plants grown in a phytotron as described before (Kvaale and Olsen, 1986). The plants were emasculated and pollinated by hand and isolated in order to ensure accurate determination of seed age.

II. cDNA and genomic clones

The isolation and sequencing of the aleurone specific cDNA clone pBz1 1E (which is the same as Ltp2) was conducted as described by Jakobsen et al. (1989).

A barley, cv. Bomi genomic library was constructed by partial MboI digestion of total genomic DNA and subsequent ligation of the 10–20 kilo basepair (kb) size fraction with BaMHI digested lambda EMBL3 DNA (Clontech Labs, Palo Alto, Calif., USA). Out of a total of $2\times10^6$ plaques screened, using the Bz1 1E cDNA insert as a template for probe synthesis with a random labelling kit (Boehringer-Mannheim), four positive clones (gHv29–101, gHv38–201, gHv53–201 and gHv59–101) were identified after repeated rounds of plaque hybridization. DNA purified from these clones were restricted with several enzymes and characterized by Southern blot analysis.

The restriction maps of the four clones showed extensive overlap. One clone, gHv53–201, containing an insert of around 12 kb, was chosen for further analysis. A 6 kb PstI fragment contained within the insert that hybridized to the cDNA probe was subcloned into Bluescript (Stratagene) giving the subclone BL53Ps17. A NheI restriction fragment of 0.7 kb covering the coding region of the Ltp2 gene was cloned into the XbaI site of M13mp18 and sequenced using the Sequenase protocol (USB) after isolation of ssDNA template using PCR amplification and magnetic beads (Dynabeads M280—Streptavidin, Dynal).

In order to characterize the 5' and 3' sequences of the Ltp2 gene, the following DNA fragments were generated by PCR amplification:

i) a 1.2 kb fragment covering the 5' end from a vector primer (KS) to the PLT11 primer located within the 5' end of the cDNA; and ii) a 0.3 kb PCR product generated by amplification directed by the primers LTP13 and PLT15, of which the latter is based upon sequence information from the cDNA clone Bz14A, which is overlapping and identical with the Bz1 1E cDNA but contains some additional 30 base pairs after the polyadenylation site indicated at position 490 in FIG. 1.

The sequences are:

| | | | | |
|---|---|---|---|---|
| KS: | 5' CGAGGTCGAC | GGTATCG | 3' | (SEQ ID NO 4) |
| PLT11: | 5' TACGGTGATC | TACTCGGCTA | 3' | (SEQ ID NO 5) |
| LTP13: | 5' ACGAAGCCGA | GCGGCGAGT | 3' | (SEQ ID NO 6) |
| PLT15: | 5' GGACTAAAAA | AAAAGTTGCA ACACAAATTT | 3' | (SEQ ID NO 7). |

The PLT11 sequence contains one base substitution (shown in bold and underlined) creating a BglII restriction site.

The 1.2 kb PCR product containing the 5' end was restricted with BglII which gave a 0.84 kb fragment with BamHI compatible sticky ends that was subsequently cloned into the BamHI site of pBluescript.

The 0.3 kb PCR product of the 3' end was treated with T4 DNA polymerase (Sambrook et al., 1989) and subsequently cloned into the SmaI site of M13mp18.

The sequences of the PCR products were determined as described above.

iii. Northern analyses

Total RNA was extracted from barley seed tissues of 10 DAP and older plant material essentially as described by Logemann et al. (1987), except that LiCl precipitation was used in place of ethanol precipitation. The RNA was denatured using formaldehyde and separated on 1.2% agarose gels as described by Selden (1987) and blotted onto Gene-Screen (NEN) membranes using a Stratagene posiblotter apparatus according to supplier's instructions.

Hybridization was according to GeneScreen instruction manual (NEN) using radioactively labelled DNA strands complementary to the pBz1 1E cDNA insert generated with a random primed DNA labeling kit (Boehringer Mannheim).

iv. In situ hybridization

For in vitro transcription of antisense RNA, the plasmid pBz1 1E (Jakobsen et al., 1989) was linearized with PstI and transcribed with T7 RNA polymerase by using MAXIscript (Ambion) and [5,6-3H]-Uridine 5'-triphosphate (40–60 Ci mmol-1) (Amersham International) according to the specifications of the suppliers. The probe was hydrolyzed to fragments of about 100 bp as described by Somssich et al. (1988). Seed tissues were fixed in 1% glutaraldehyde, 100 mM sodium phosphate (pH 7.0) for 2 hours and embedded in Histoplast (Histolab, Göteborg, Sweden).

Sections of 10 μm were pretreated with pronase (Calbiochem) as described by (Schmelzer et al., 1988) and hybridized with 25 ml of hybridization mix (200 ng probe ml-1, 50% formamide, 10% (w/v) dextran sulphate, 0.3 M NaCl, 10 mM Tris-HCl, 1 mM EDTA (pH 7), 0.02% polyvinylpyrrolidone, 0.2% Ficoll, 0.02% bovine serum albumin) for 15 hours at 50° C.

Posthybridization was carded out according to Somssich et al. (1988) and autoradiography was done as described by Schmelzer et al. (1988), except that sections were exposed for 10 weeks.

v. Constructs for transient expression analysis

For the microprojectile bombardment experiments, the following constructs were used:

CONTROL A: pAct1f-GUS containing the rice Actin 1 promoter fused to the uidA reporter gene encoding the GUS enzyme (McElroy et al., 1990);

CONTROL B: pRT101-ex/s-int/s-LUC containing the 35S CaMV promoter-Sh1 first exon/intron fused to the firefly luciferase gene (Maas et al., 1991); and CONTROL C: pRT101C1 containing the C1 cDNA downstream of the 35S CaMV promoter (Paz-Ares et at., 1987);

CONTROL D: pMF6Lc(R) containing the Lc cDNA corresponding to one R gene allele coupled to the 35S CaMV promoter-Adh1 intron (Ludwig et al., 1989). p For the transient expression studies in barley aleurone the first intron of the maize Sh1 gene carded on a 1.1 kb HincII fragment (Maas et al., 1991) was inserted into the SmaI site of the promoter-reporter gene constructs according to the present invention. The Ltp2 gene promoter is contained on the 0.84 kb BglII fragment (sequence is presented in FIG. 2) and was inserted into the BamHI site of pBluescript. Thereafter the structural uidA gene encoding the beta-glucuronidase (Gus) enzyme was fused to the Ltp2 gene promoter.

The following conjugates according to the present invention were studied:

(i) Ltp2/GN: A Ltp2 gene promoter—GUS conjugate (same as conjugate in pLtp2/GN—see earlier);

(ii) Ltp2Sh1/GN: A Ltp2 gene promoter—Sh1 intron—GUS conjugate (same as conjugate in pLtp2Sh1/GN- see earlier).

Isolated plasmid DNA was used in the bombardment studies. The same conditions were used for the control conjugates and for the conjugates of the present invention.

For transient assay studies with rice protoplasts, the following conjugates according to the present invention were studied:

(i) Ltp2/GN: As above; and (iii) Ltp2ΔBCIGN: A Ltp2 gene promoter {with a deletion spanning the myb and myc sites}—GUS conjugate (same as conjugate in pLtp2ΔBCIGN—see earlier).

vi. Transformation of barley aleurone layers by particle bombardment

Barley seeds were harvested at 25 DAP, surface sterilized in 1% sodium hypochlorite for 5 min and then washed 4 times in sterile distilled water. The maternal tissues were removed to expose the aleurone layer and the seed was then divided into two, longitudinally along the crease. The pieces of tissue were then placed, endosperm down, onto MS (Murashige & Skoog 1962) media with 10 g/l sucrose solidified with 10 g/l agar in plastic petri dishes (in two rows of 4 endosperm halves per dish).

Single bombardments were performed in a DuPont PDS 1000 device, with M-17 tungsten pellets (approx. 1 μm in diameter) coated with DNA as described by Gordon-Kamm et al. (1990) and using a 100 mm mesh 2 cm below the stopping plate. Equal amounts (25 μg per preparation) of the GUS (promoter-reporter gene) and LUC (internal standard) plasmids were mixed before adding the microprojectiles. One tenth of this amount, 2.5 μg, was used for the Lc and C1 cDNA constructs. Bombarded tissue was incubated at 24° C. for 3–4 days before extraction and measurement of GUS and LUC activities. Anthocyanin pigmentation could be observed in the bombarded aleurones directly without further treatment. Histochemical staining for GUS expression was performed with X-Gluc (5-bromo,4-chloro,3-indolyl,β-D,Glucuronic acid) as described by Jefferson (1987) at 37° C. for 2 days. Extraction of cellular proteins for quantitative analysis was performed by grinding 4–8 half seeds in a mortar and pestle with 0.5 ml of extraction buffer (50 mM Na-phosphate pH, 1 mM DTT, pH 7.0).

After grinding, a further 0.5 ml was added and two 400 μl aliquots were taken. To one of these, 100 μl of 5×Luciferase cell lysis buffer (Promega) was added and the sample vortexed before clearing by centrifugation at 10,000 rpm. A 20 μl aliquot was then measured for LUC activity in a scintillation counter (Tri-Carb 4000), using the luciferase assay system of Promega (E1500). To the other 400 μl aliquot, 100μl of 5×lysis buffer (500 mM Na phosphate pH 7.0, 50 mM EDTA, 10 mM DTT, 0.5% Sarcosyl, 0.5% Triton X-100) was added, the mixture vortexed and cleared as above and assayed for GUS activity using 4-methylumbelliferone, β-D,glucuronide as described by Jefferson (1987) modified to include 5% methanol in the reaction mixture (Kosugi et at., 1990).

Production of 4-methylumbelliferone (MU) was measured after 1 and 4 h using a TKO 1000 Mini-Fluorimeter (Hoefer Scientific Instruments). In the analysis of promoter activities, the GUS readings (MU produced per hr) were standardized by division with the LUC value (photons produced over 30 s, beginning 60 s after mixing) from the same extract.

vii. Transient assay of rice protoplasts

In this experiment, the same type of protoplasts as used for stable transformation of rice plants was transiently transformed with constructs (i) and (iii) (see above) and then assayed for GUS activity.

viii. Rice transformation

Southern blot analysis of transgenic rice plants

Total genomic DNA was isolated from mature leaves, digested with Xba I and then transferred to a nylon membrane (Amersham). The coding region of the GUS gene was labelled and amplified with digoxigenin 11-dUTP by polymerase chain reaction and used for probing the Ltp2—GUS gene. Hybridization and chemiluminesence signal detection were performed according to manufacturers specifications (Boeringen Mannheim).

B. RESULTS WITH REFERENCE TO THE FIGURES i. FIG. 1 is a nucleotide sequence of the LIp2 gene (SEQ ID No. 3). A transcription start site has been assigned as +1. The TATA consensus sequence is boxed. Consensus myb and myc binding sites and the SphI element (Hattori et al., 1992) found in the C1 promoter sequence are shown in bold italics.

In the ORF (open reading frame), the nucleotides are shown in bold letters, starting with the first ATG codon and ending with the TAG stop codon. The single base substitution introduced at position +41 (A>T) creates a BglII restriction site which delimits the 3' end of the fragment covering the Ltp2 gene promoter. The positions of the 5' end and polyadenylation site of the corresponding cDNA, Bz1 1E (Jakobsen et al., 1989), are shown by arrows. Two putative polyadenylation signals are underlined.

ii. FIG. 2a is a nucleotide sequence for the Ltp2 gene promoter (SEQ ID No. 1). FIG. 2b is a nucleotide sequence for the Ltp2 gene promoter with an additional number of nucleotides for fusion to a GUS gene.

iii. FIG. 3 shows transverse sections from the mid-region of barley seeds (A-E) and steady state levels of the Ltp2 mRNA in different tissue fractions of developing barley endosperm (F).

FIG. 3 can be analysed as follows:

(A): Ten DAP (days after pollination) endosperm isolated from the surrounding maternal tissues by manual extrusion. For maternal tissues, see (C). The extruded endosperm consists of the central starchy endosperm cells, a group of modified aleurone cells over the crease area (arrow) and one layer of highly vacuolated peripheral aleurone cells (arrowhead).

(B): Enlargement showing vacuolated peripheral aleurone cells (AC) and starchy endosperm cells (SE) in area of (A) marked with arrowhead.

(C): Pericarp of 10 DAP seed after extrusion of the endosperm with the nucellus epidermal layer (NE) facing the endosperm cavity, which contained the endosperm in (A) before extrusion.

(D): Extruded 15 DAP endosperm with central starchy endosperm cells and modified aleurone cells (arrow), but without peripheral aleurone cells.

(E): 15 DAP pericarp with adhering aleurone layer after extrusion of the endosperm (in D).

Figure 4:
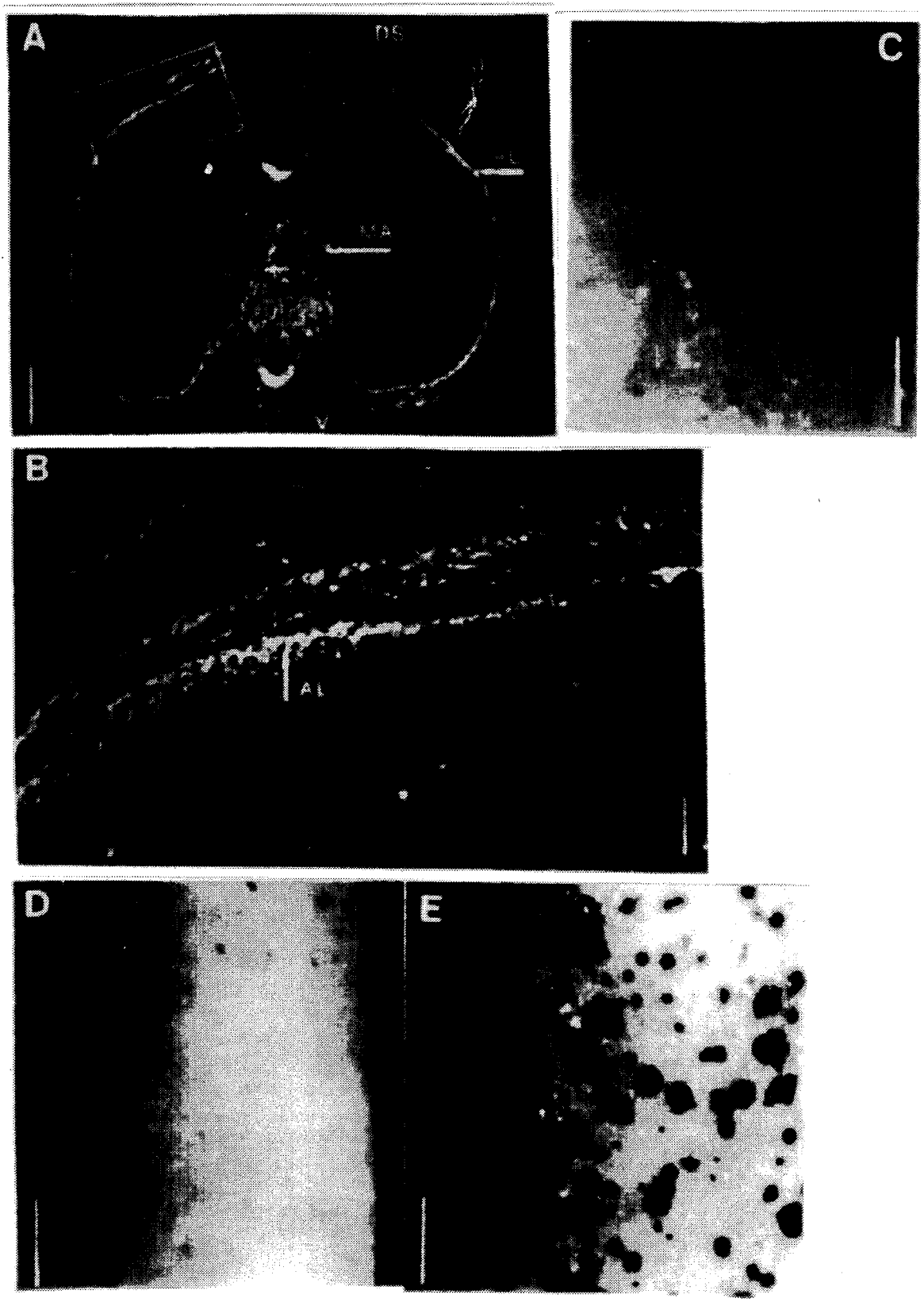
FIG. 4 shows the results for an in situ hybridization experiment.

(F): Northern blot showing the steady state level of Ltp2 mRNA in the extruded endosperm fraction (e) and the pericarp fraction (p) in the interval from 10 to 13 DAP. For this blot, 10 μg of total RNA was loaded in each lane. The gel was blotted and hybridized with randomly primed Ltp2 cDNA.

iv. FIG. 4 shows the results for an in situ hybridization of $^3$H-labelled Ltp2 antisense probe to transverse sections of barley endosperm (A and B) and transient gene expression analysis of different promoter-reporter gene constructs in developing barley aleurone layers after particle bombardment (C, D and E). FIG. 4 can be analysed as follows:

(A): Dark field microphotograph of 13 DAP endosperm showing hybridization of the Ltp2 probe to the peripheral aleurone cells (AL) ventrally and laterally, but not to aleurone cells on the dorsal side of the grain (DS), nor to the modified aleurone cells over the crease area (MA).

(B): Magnification of peripheral endosperm (frame in A) showing gradient of in situ hybridization signal towards the dorsal side of the seed containing undifferentiated aleurone cells.

(C): Colourless barley aleurone layer co-bombarded with the 35S-C1 and 35S-Lc cDNA constructs. Single aleurone cells synthesizing anthocyanin pigment appear as red spots.

(D): Exposed aleurone layer of 25 DAP barley seeds bombarded with the Ltp2/Sh1 int/GUS construct. The transfected seed was stained for detection of GUS activity.

(E): Exposed aleurone layer of barley seed of the same stage bombarded with pAct1f-GUS construct and histochemically stained as in (D).

Figure 5:
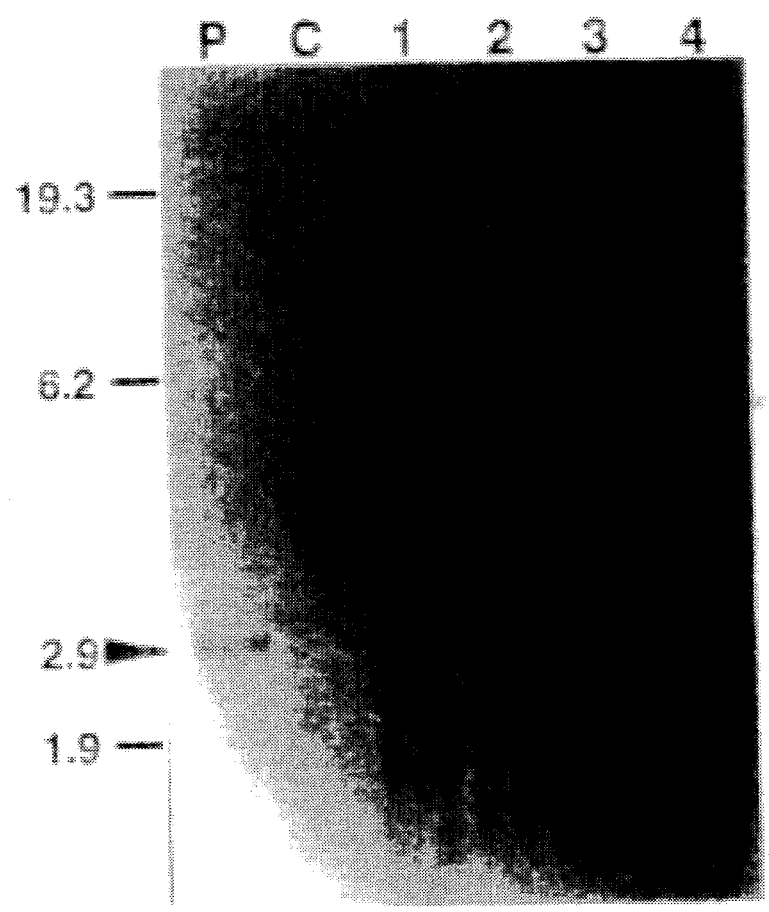
FIG. 5 is the result of a Southern blot experiment using DNA from transgenic rice plants.

(V): Ventral crease area.

v. FIG. 5 is the result of a Southern blot experiment of DNA from transgenic rice plants harbouring the Ltp2-GUS construct. FIG. 5 can be analysed as follows:

Lane P: plasmid Ltp2-GUS.

Lane C: untransformed control plants.

Lane 1: transgenic line 3–15.

Lane 2: transgenic line 4–13.

Lane 3: transgenic line 2–6.

Figure 6:
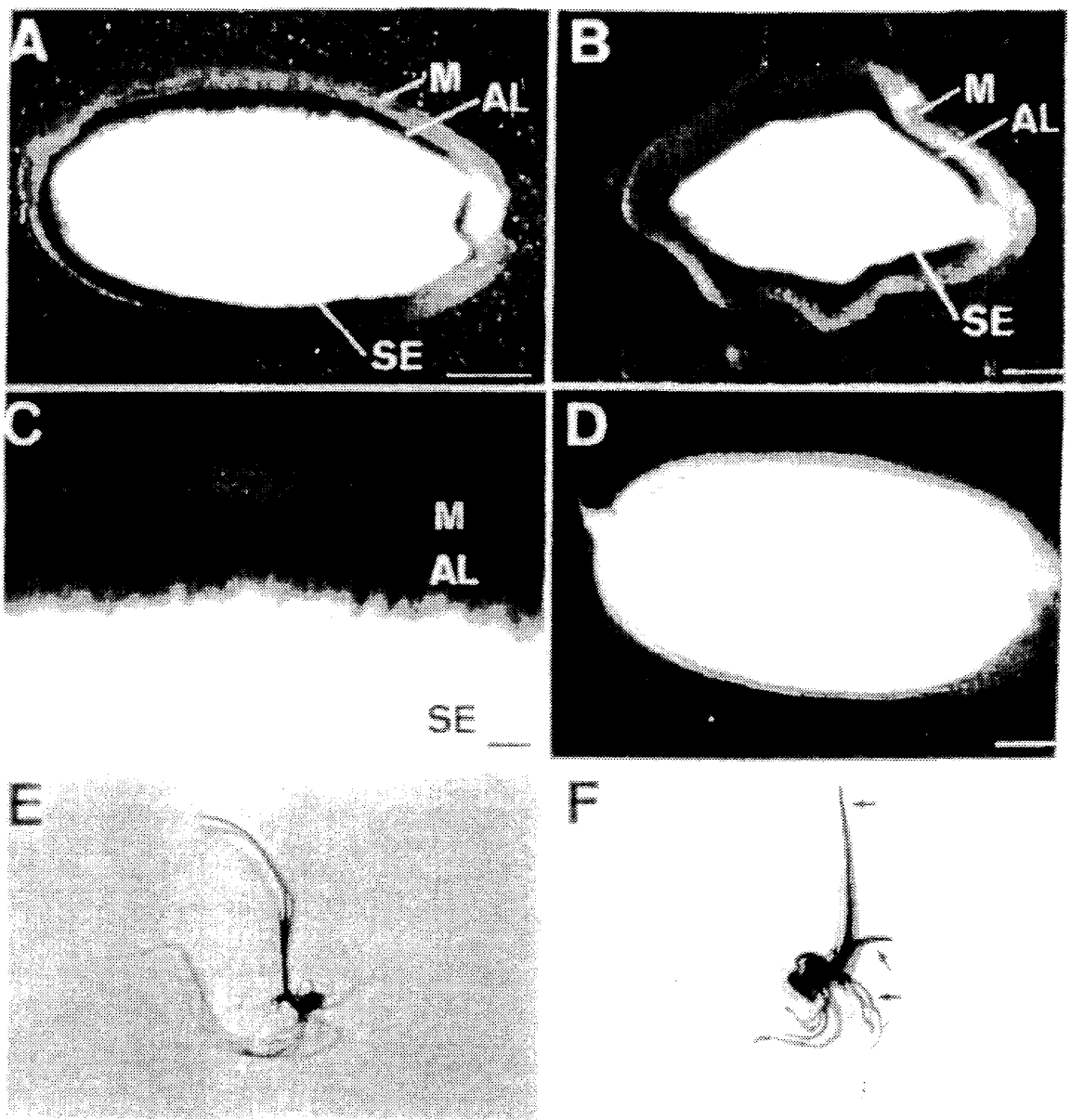
FIG. 6 shows the expression of a GusA-reporter gene driven by the Ltp2 gene promoter in the aleurone layer of developing transgenic rice seeds.

Lane 4: transgenic line 4–6.

vi. FIG. 6 shows the expression of a GUS-reporter gene driven by the Ltp2-wildtype promoter in the aleurone lawyer of developing transgenic rice seeds. FIG. 6 can be analysed as follows:

(A): Longitudinal section of 20 DAP seed showing GUS staining exclusively in the aleurone layer (AL), but not in the embryo, starchy endosperm (SE) or in the maternal tissue (M).

(B): Transverse section from the mid-region of 20 DAP seed.

(C): Enlargement of dorsal side of seed shown in (A).

(D): Non-transgenic control seed, same age as in (A).

(E): A 5 day-old seedling transformed with the Ltp2—GUS gene.

(F): A 5 day-old seedling transformed with the CaMV35S—GUS gene. (Terada and Shimamoto 1990). Arrows indicate regions of GUS expression. Bars in (A,B and D) are 10 mm and in (C) 2.5 mm.

vii. FIG. 7 shows the position of the myb and myc sites in the barley Ltp2 gene promoter. The distance from the 3' end of the myc site to the TATA box is given in nucleotides.

The following nucleotides from and between the myb and myc sites were deleted to form the conjugate containing the deletion in the Ltp2 gene promoter gene:

CAACTACCATCGGCGAACGACCCAGC.

C. CONCLUSIONS

1. The barley Ltp2 gene encodes a protein homologous to the 7 kDa wheat lipid transfer protein Using the Bz1 1E cDNA (Jakobsen et al., 1989) as a probe, the corresponding barley cv. Bomi genomic clone was isolated. The sequences of the genomic clone and that of the Bz1 1E cDNA are identical in overlapping regions and no intervening sequences were detected (FIG. 1) accordingly this gene is Ltp2. The ATG codon initiating the longest open reading frame (ORF) in the Ltp2 sequence is located 64 bp downstream of the putative transcriptional start site at nucleotide number 1 (FIG. 1). The ORF contains eight potential translation start codons between nucleotides 64 and 127. Two polyadenylation signals, which conform to the plant consensus sequence (Joshi, 1987) are found in the 3' end of the genomic sequence. In the Bz1 1E cDNA the poly A tail extends after the G at position 491 (FIG. 1 and FIG. 2).

2. The LIp2 transcript can be a molecular marker for peripheral aleurone cell differentiation In the developing seed at approximately 8 days after pollination (DAP), aleurone cell differentiation is initiated over the ventral crease area resulting in the formation of the modified aleurone cells (FIG. 3A and Bosnes et al., 1992). Shortly after, at 9 DAP, the second type of aleurone cells, characterized by their extensive vacuolation (FIG. 3B), appears in the peripheral endosperm close to the crease area, spreading first laterally and then to the dorsal side of the seed (see FIG. 3A). At this stage, when whole deembryonated seeds are squeezed, the extruded endosperm consists of the starchy endosperm, the peripheral and the modified aleurone cells (FIG. 3 A-C). This is in contrast to later developmental stages, where the extruded endosperm consists only of the starchy endosperm and the modified aleurone cells (FIG. 3D). The reason for this is that the cells of the aleurone layer adhere to the maternal pericarp (FIG. 3E). Aleurone cell formation is completed at 21 DAP, when cell division stops (Kvaale and Olsen, 1986). Using the Ltp2 probe on Northern blots with total RNA, the signal obtained gradually becomes stronger in the pericarp, compared to the extruded endosperm, confirming the relocation of the aleurone cells from the endosperm fraction to the pericarp fraction in the interval between 10 and 13 DAP (FIG. 3F).

From the experimental results presented in FIG. 3 it is concluded that the Ltp2 transcript is a potential marker for aleurone cell differentiation. To corroborate the usefulness of the Ltp2 transcript as a molecular marker for aleurone cell differentiation, in situ analysis was carded out on transverse sections of 13 DAP seeds. The rationale for using seeds from this stage was the earlier observed gradual differentiation of the peripheral aleurone cells, starting near the crease area and spreading to the dorsal side (Bosnes et al., 1992).

Using $^3$H-labelled antisense transcript as probe, a positive signal is clearly visible in the peripheral aleurone cells in the ventral part adjacent to the crease area as well as laterally up towards the dorsal side of the grain (FIG. 4A). However, no signal is present in the dorsal region of the seed, nor over the modified aleurone cells.

Focusing on the most dorsal aleurone cells showing a positive signal in the in situ analysis (FIG. 4B), the morphology of these cells corresponds to that of the highly vacuolated peripheral aleurone cells in 10 DAP endosperm (FIG. 3B).

The Ltp2 transcript therefore represents a highly tissue specific molecular marker for aleurone cell differentiation.

3. The Ltp2 gene promoter is transiently expressed in developing barley aleurone cells after particle bombardment The Ltp2 gene promoter contained on a 842 bp BglII restriction fragment (from nt −807 to nt+35 in FIG. 1) was fused to the GUS-reporter gene and introduced into the exposed aleurone layers of 25 DAP whole barley seeds by the biolistic method. In the first set of experiments, Ltp2 gene promoter activity was assayed visually after histochemical staining with X-Gluc. Due to the large variation between individual experiments with the biolistic method, plasmid DNA containing the Lc and C1 cDNAs from maize under the control of the 35S CaMV promoter was co-bombarded with the Ltp2 construct to monitor shooting efficacy. In combination, but not individually, the latter two cDNAs give high numbers of red anthocyanin spots in the barley aleurone cells without any treatment after 1 to 2 days of incubation of the seeds on solid nutrient medium (FIG. 4C). Compared to the number of red spots, the Ltp2-GUS construct consistently gave very few spots after histochemical staining in co-bombardment experiments.

Based on previous reports that insertion of introns in promoter construct enhance the level of transient expression (Maas et at., 1991) without interfering with the tissue specificity of the promoters, the intron from the maize Shrunken-1 gene was inserted into the Ltp2-GUS construct after the promoter. Using this construct the number of spots in immature aleurone layers increased (FIG. 5D). Still, however, compared to aleurone layers bombarded with the pAct1f-GUS construct (McElroy et al., 1990), which contains the promoter of the constitutively expressed Actin1 gene from rice (FIG. 4D), both the number and the size of the spots obtained with the Ltp2-GUS construct is dramatically smaller (FIG. 4E).

In order to quantify Ltp2 gene promoter activity in particle bombardment experiments, another control plasmid containing the LUC gene under the control of the 35S-promoter was co-bombarded with the Ltp2-GUS constructs. In this way, after particle bombardment and incubation on tissue culture medium, protein was extracted from the seeds in a buffer that allowed measurement of both LUC and GUS activity (for details, see Materials and Methods section). In such experiments, calculating GUS expression standardized on the base of the LUC-activity, the Ltp2-GUS activity was not significantly higher than background, corresponding approximately to 1.5% of the Actin1f promoter activity in parallel experiments.

For the Ltp2-Sh1 intron-GUS construct, however, the activity was significantly higher than background, corresponding to 5 % of that of the Actin1 promoter. Blue spots from the activity of the Ltp2-promoter were never observed in other tissues than the aleurone layer of developing seeds. From these experiments it is concluded that the −807 bp promoter of the Ltp2 gene is capable of directing transient gene expression in a fashion similar to that of the endogenous Ltp2 gene, i.e., in the cells of the aleurone layer of immature barley seeds.

4. The Ltp2 gene promoter directs aleurone specific expression of the GUS-reporter gene in transgenic rice seeds The gene was transformed into rice by electroporation of embryogenetic protoplasts following the teachings of Shimamoto et at. 1989.

Four fertile transgenic rice plants were obtained and integration of the Ltp2-GUS gene was examined by Southern blot analysis. The results demonstrated that a 2.9 b fragment containing the Ltp2-GUS gene is integrated in all the transgenic lines. Histochemical GUS analysis was carried out with developing rice seeds of 20 DAP and 5 day old seedings derived from transgenic seeds (FIG. 6). In developing seeds the GUS expression is strictly limited to the aleurone layer, with no staining observed in the maternal tissues, starchy endosperm or in the embryo of the transgenic seeds (FIG. 6 A–C), nor in untransformed control seeds (FIG. 6 D). No GUS staining was observed in leaves or roots of seedlings transformed with the Ltp2 - GUS gene (FIG. 6 E).

In contrast, seedlings transformed with the CaMV35S - GUS gene GUS expression is detected in the coleptile, shoots and roots (see FIG. 6 F; Terada and Shimamoto 1990).

These results clearly demonstrate the aleurone-specific expression of the Ltp2 - GUS gene in transgenic rice plants.

5. The Ltp2 gene promoter contains sequence elements implicated in the transcriptional control of cereal endosperm specific genes The studies with the deletion spanning the myb and myc sites in the Ltp2 gene promoter showed that levels of expression were about 10% of that of the wild-type gene promoter.

These studies indicated that both the myb and myc sites are important for expression.

In addition, the Ltp2 gene promoter may even contain another sequence element that has been implicated in regulation of gene expression in maize aleurone cells, namely the octanucleotide CATGCATG (FIG. 1 residues 717–724 of SEQ ID No. 1). This sequence, previously referred to as the SphI element, has been shown to mediate the transcriptional activation of maize C1 by interaction with VP1 (Hattori et al., 1992). As in the maize C1 promoter (Paz-Ares et al., 1987), the putative SphI element of the barley Ltp2 gene promoter is located between the TATA-box and the myb binding site.

In addition, the Ltp2 gene promoter may contain two further sites that could play an important role in transcription. The first site is an "AL" site and has the sequence (corresponds to residues 435 to 442 of SEQ ID No. 1).

CATGGAAA

This AL sequence ends at position −366 in the sequence shown in FIG. 1.

The second site is a "DS" site that has a high degree of similarity or identity with the binding site for 5' transcriptional factors from other eucaryotic organisms. This DS site, which a dyad-symmetry, has the sequence (corresponding to residues 675 to 687 of SEQ ID No. 1).

TCGTCAGCGACGA

This DS sequence ends at position −121 in the sequence shown in FIG. 1.

D. DISCUSSION

The above examples of the present invention concern the barley gene Ltp2, which encodes an aleurone specific 7 kDa nsLTP.

The identification of the Ltp2 protein as a nsLTP is based on the high identity (78% ) between the predicted Ltp2 amino acid sequence and the 7 kDa protein isolated from wheat seeds using the in vitro lipid transfer assay (Monnet, 1990). The high degree of sequence identity between the two barley aleurone Ltp gene products and the homologous proteins and transcripts from wheat seeds strongly suggests that the aleurone layer of these two cereals contain two related classes of nsLTPs with molecular masses of 10 and 7 kDa, respectively.

While the sequence identity is more than 70% within the two classes, it is only around 20% between them. However, several conserved features are apparent in the cereal seed nsLtps, including similar N-terminal signal peptides, an internal stretch of 20 amino acids with 60% similarity, and 8 cysteine residues that are believed to be important for the activity of plant Ltps (Tchang et al., 1988). Studies also showed that the Ltp2 gene lacks an intron. Hybridization experiments using Ltp2 probes to barley genomic Southern blots indicate that the barley haploid genome contains only one copy of each gene (Jakobsen et al., 1989; Skriver et al., 1992).

According to a suggestion by Sterk et al. (1991) plant nsLTPs may be involved in the extracellular transport of cutin or other lipid monomers from the endoplasmic reticulum to the site of synthesis of extracellular matrix components, such as the cuticle. Therefore, one possible role for the aleurone specific nsLTPs in barley and wheat could be in the formation of the earlier described amorphous layer on the outside of the aleurone cells in wheat seeds (Evers and Reed, 1988). The function of this layer is unknown, but it may be involved in the regulation of the osmotic pressure in the endosperm during seed development and germination. If this holds true, the absence of the Ltp2 transcript in the modified aleurone cells in the ventral crease area is functionally significant, since an impermeable layer on the outside of these cells would prevent the influx of soluble synthates from the vegetative plant parts.

Of the nine cDNAs isolated in the differential screening experiment design to identify clones representing transcripts differentially expressed in the aleurone layer of developing barley seeds, Ltp2 hybridizes to transcripts present exclusively in the aleurone layer. Thus, the Ltp2 gene represents a suitable gene for the search for promoter sequences responsible for the control of gene transcription in the aleurone layer.

Due to the lack of a routine protocol for stable barley transformation, demonstration of Ltp-promoter specificity in barley has to rely on transient assays using the particle bombardment method. Using this method, it was demonstrated that the −807 bp Ltp2 gene promoter carried on the BglII restriction fragment is capable of driving the expression of the GUS reporter gene in immature barley aleurone layers. From this it is concluded that the promoter fragment carries sequences that are responsible for barley aleurone specific gene transcription.

The Ltp2 gene promoter can be weaker than constitutive cereal promoters like that of the Actin1f gene-even after the introduction of the Sh1-intron (see Maas et al. (1991) and their work on tobacco protoplasts) into the Ltp2-GUS construct which increases the expression levels by around three-fold. However, this lower expression does not result in any damage to the developing seedling - unlike the constitutive cereal promoters. Moreover, and again unlike the constitutive cereal promoters, the Ltp2 gene promoter directs desirable tissue and stage specifc expression.

As demonstrated by the histochemical assays shown in FIG. 6, the Ltp2 BglII promoter fragment shows the same aleurone specific expression in developing rice seeds as in barley.

Thus, the conclusion from the transient assays in barley that this promoter fragment contains sequences responsible for aleurone specific gene transcription is confirmed. Furthermore, the data from rice provide support to the view that the molecular mechanisms underlying aleurone specific gene transcription in developing seeds are conserved among the cereal species.

E. SUMMATION

The Examples describe the isolation of the promoter for the barley gene Ltp2, which encodes a novel class of cereal 7 kDa nsLTPs. The gene was isolated by the use of a cDNA from a differential screening experiment in which the positive probe was constructed from aleurone cell poly (A) rich RNA, and the negative probe from the starchy endosperm of immature seeds.

In situ hybridization analysis demonstrates that the Ltp2 transcript is expressed exclusively in the aleurone layer from the beginning of the differentiation stage and half way into the maturation stage. Similar to previously identified 10 kDa plant nsLTPs, the Ltp2 protein contains the eight conserved cysteine residues.

The results indicate that the Ltp2 protein is involved in the synthesis of a lipid layer covering the outside of the cereal aleurone cells.

Using particle bombardments it was shown that the −807 bp Ltp2 gene promoter fused to the GUS-reporter gene is active in the aleurone layer of developing barley seeds, giving 5% of the activity of the strong constitutive actin 1 f-promoter from rice. Transformed into rice, the barley Ltp2-promoter directs strong expression of the GUS-reporter gene exclusively in the aleurone layer of developing rice seeds. Analysis of the Ltp2 gene promoter reveals the presence of sequence motives implicated in endosperm specific gene expression in maize, i.e. the myb and myc protein binding sites. In short, the Ltp2 gene promoter represents a valuable tool for the expression of GOIs in the aleurone layers of cereal seeds.

Other modifications of the present invention will be apparent to those skilled in the art without departing from the scope of the invention.

REFERENCES

Baker, R. E., Gabrielsen, O. S., and Hall, B. D. (1986) Effects of tRNATyr point mutations on the binding of the yeast RNA polymerase III transcription factor C. *J. Biol. Chem.* 261, 5275–5282.

Barkardottir, R. B., Jensen, B. F., Kreiberg, J. D., Nielsen, P. S. and Gausing, K. (1987) Expression of selected nuclear genes during leaf development in barley. *Dev. Genet.* 8, 495–511.

Bosnes, M., Weideman, F. and Olsen, O.-A. (1992) Endosperm differentiation in barley wild-type and sex mutants. *Plant J.* 2, 661–674.

Dellaporta, S. L., Greenblatt, I., Kermicle, J. L., Hick, J. B. and Wessler, S. (1988) Molecular cloning of the R-nj allelel by transposon tagging with Ac. In *Chromosome structure and function: Impact of new concepts,* 18th Stadler Genetics Symposium (Gustafson, J. P. and Appels, R., eds.), New York: Plenum Press, pp. 263–282.

Dieryck, W., Gautier, M.-F., Lullien, V. and Joudrier, P. (1992) Nucleotide sequence of a cDNA encoding a lipid transfer protein from wheat (*Triticum durum*Desf.). *Plant Mol. Biol.* 19, 707–709.

Dooner, H. K. (1983) Coordinate genetic regulation of flavonoid biosynthetic enzymes in maize. *Mol. Gen. Genet.* 198, 136–14.

Dooner, H. K. (1985) *Viviparous* −1 mutation in maize conditions pleiotropic enzyme deficiencies in the aleurone. *Plant Physiol.* 77, 486–488.

Evers, A. D. and Reed, M. (1988) Some novel observations by scanning electron microscopy on the seed coat and nucellus of the mature wheat grain. *Cereal Chem.* 65, 81–85.

Fincher, G. B. (1989) Molecular and cellular biology associated with endosperm mobilization in germinating cereal grains. *Annu. Rev. Plant Physiol. Plant Mol. Biol.* 40, 305–346.

Fleming, A. J., Mandel, T., Hofmann, S., Sterk, P., de Vries, S. C., and Kuhlemeier, C. (1992) Expression pattern of a tobacco lipid transfer protein gene within the shoot apex. Plant J. 2, 855–862.

Franken, P., Niesbach-Kløsgen, U., Weydeman, U., Marechal-Drouard, L., Saedler, H., and Wienand, U. (1991). The duplicated chalcone synthase genes C2 and Whp (white pollen) of Zea mays are independently regulated; evidence for translational control of Whp expression by the anthocyanin intensifying gene. *EMBO J.* 10, 2605–2612.

Friedman, W. E. (1992) Evidence of a pre-angiosperm origin of endosperm: implication for the evolution of flowering plants. *Science* 255, 336–339.

Gabrieisen, O. S., Sentenac, A. and Fromageot, P. (1991) Specific DNA binding by cMYB: Evidence for a double helix-turn-helix-related motif. *Science,* 253 1140–1143.

Goff, S.A., Cone, K. C. and Chandler, V. L. (1992) Fuctional analysis of the transcriptional activator encoded by the maize B gene: evidence for a direct functional interaction between to classes of regulatory proteins. *Genes Dev.* 6, 864–875.

Gordon-Kamm, W. J., Spencer, T. M., Mangano, M. L., Adams, T. R., Daines, R. J., Start, W. G., O'Brien, J. V., Chambers, S. A., Adams, W. R., Willetts, N. G., Rice, T. B., Mackey, C. J., Krueger, R. W., Kausch, A. P. and Lemaux, P. G. (1990) Transformation of maize cells and regeneration of fertile transgenie plants. *Plant Cell* 2, 603–618.

Hammond-Kosack, M. C. U., Holdsworth, M. J. and Bevan, M. (1993) In vivo footprinting of a low molecular weigth glutenin gene (LMWG-1D1) in wheat endosperm. *EMBO J.* 12, 545–554.

Hattori, T., Vasil, V., Rosenkrans, L., Hannah, L. C., McCarty, D. L. and Vasil, I. K. (1992) The Viviparous-1 gene and abscisic acid activate the C1 regulatory gene for anthocyanin biosynthesis during seed maturation in maize. *Genes Dev.* 6, 609–618.

Jacobsen, J. V., Knox, R. B. and Pyliotis, N. A. (1971) The structure and composition of aleurone grains in the barley aleurone layer. *Planta* 101, 189–209.

Jakobsen, K., Klemsdal, S., Aalen, R., Bosnes, M., Alexander, D. and Olsen, O.-A. (1989) Barley aleurone cell development: molecular cloning of aleurone-specific cDNAs from immature grains. *Plant Mol. Biol.* 12, 285–293.

Jefferson, R. A. (1987) Assaying chimeric genes in plants: the GUS gene fusion system. *Plant Mol. Biol. Rep.* 5, 387–405.

Joshi, C. P. (1987) Putative polyadenylation signals in nuclear genes of higher plants: a compilation and analysis. *Nucleic Acid Res.* 15, 9627–9640.

Kalla, R., Lonneborg, A., Linnestad, C., Potter, R., Aalen, R., Nielsen, P. S. and Olsen, O.-A. (1993) Characterisation of promoter elements of aleurone specific genes from barley. In Pre-harvest sprouting in cereals 1992. Eds. M. K. Walker-Simmons and J. J. Ried. The American Association of Cereal Chemists, Inc. ISBN 0-913250-81-3. pp. 236–245.

Karrer, E. J., Litts, J. C. and Rodriguez, R. L. (1991) Differential expression of a-amylase genes in germinating rice and barley seeds. *Plant Mol. Biol.* 16, 797–805.

Kader, J.-C., Julienne, M. and Vergnolle, C. (1984) Purification and characterisation of a spinach-leaf protein capable of transferring phospholipids from liposomes to mitochondria or chloroplasts. *Eur. J. Biochem.* 139, 411–416.

Koltunow, A. M., Truettner, J., Cox, K. H., Wallroth, M. and Goldberg, R. B. (1990) Different temporal and spatial expression patterns occur during anther development. *Plant Cell* 2, 1201–1224.

Kosugi, S., Ohashi, Y., Nakajima, K. and Arai, Y. (1990) An improved assay for b-glucuronidase in transformed cells: methanol almost completely suppresses a putative endogenous b-glucuronidase activity. *Plant Sci.* 70, 133–140.

Kvaale, A. and Olsen, O.-A. (1986) Rates of cell division in developing barley endosperms. *Ann. Bot.* 57, 829–833.

Kyozuka, J. and Shimamoto, K. (1991) Transformation and regeneration of rice protoplasts. In Plant Tissue Culture Manual B1 (Lindsey, K., ed.) Dordrecht: Kluwer Academic Publishers, pp. 1–6.

Kyozuka, J., Fujimoto, H., Izawa, T. and Shimamoto, K. (1991). Anaerobic induction and tissue-specific expression of maize Adh 1 promoter in transgenic rice plants and their progeny. *Mol. Gen. Genet.* 228, 40–48.

Lanahan, M. B., Ho, T-H. D., Rogers, S. and Rogers, J. (1992) A Gibberellin response complex in cereal a-amylase gene promoters. *Plant Cell* 4, 203–211.

Lea, R., Tommerup, H., Svendsen, I. and Mundy, J. (1991) Biochemical and molecular characterization of three barley seed proteins with antifungal properties. *J. Biol. Chem.* 266, 1564–73.

Linnestad, C., Lijnneborg, A., Kalla, R. and Olsen, O.-A. (1991) The promoter of a lipid tranfer protein gene expressed in barley aleurone cells contains similar Myb and Myc recognition sites as the maize Bz-McC allele. *Plant Physiol.* 97, 841–843.

Logemann, J., Schell, J. and Willmitzer, L. (1987) Improved method for isolation of RNA from plant tissues. *Anal. Biochem.* 163, 16–20.

Ludwig, S. R., Habera, L. F., Dellaporta, S. L. and Wessler, S. R. (1989) Lc, a member of the maize R gene family responsible for tissue-specific anthocyanin production, encodes a protein similar to transcriptional activators and contains the myc-homology region. *Proc. Natl. Acad. Sci. USA* 86, 7092–7096.

Maas, C., Laufs, J., Grant, S., Korfhage, C. and Werr, W. (1991) The combination of a novel stimulatory element in the first exon of the maize shrunken-1 gene with the following intron1 enhances reporter gene expression up to 1000 fold. *Plant. Mol. Biol.* 16, 199–207.

Madrid, S. M. (1991) The barley lipid transfer protein is targeted into the lumen of the endoplasmic reticulum. Plant Physiol. Biochem. 29, 695–703.

Marocco, A., Wissenbach, M., Becker, D., Paz-Ares, J., Saedler, H. and Salamini, F. (1989) Multiple genes are transcribed in Hordeum vulgare and Zea mays that carry the DNA binding domain of the myb oncoproteins. *Mol. Gen. Genet.* 216, 183–187.

McCarty, D. R., Carson, C. B., Stinard, P. S. and Robertson, D. S. (1989) Molecular analysis of Viviparous-1: An abscisic acid-insensitive mutant of maize. *Plant Cell* 1, 523–532.

McCarty, D. R., Hattori, T., Carson, C. B., Vasil, V., Lazar, M. and Vasil, I. K. (1991) The Viviparous-1 developmental gene of maize encodes a novel transcriptional activator. *Cell* 66, 895–905.

McClintock, B. (1978) Development of the maize endosperm as revealed by clones. In The clonal basis of development (Subtelny, S. and Sussex, I. M., eds.), New York: Academic Press, pp.217–237.

McElroy, D., Zhang, W., Cao, J. and Wu, R. (1990) Isolation of an efficient actin promoter for use in rice transformation. *Plant Cell* 2, 163–171.

Monnet, F.-P. (1990) Ph.D thesis. Universite des Sciences et Techniques du Languedoc, Montpellier, France, p. 121.

Mundy, J. and Rogers, J. (1986) Selective expression of a probable amylase/protease inhibitor in barley aleurone cells: comparison to the barley amylase/subtilisin inhibitor. *Planta* 169, 51–62.

Murashige, T., and Skoog, F. (1962) A revised medium for rapid growth and bioassays with tobacco tissue cultures. *Physiol. Plant.* 15, 473–497.

Olsen, O.-A., Potter, R. H. and Kalla, R. (1992) Histodifferentiation and molecular biology of developing cereal endosperm. *Seed Sci. Res.* 2, 117–131.

Paz-Ares, J., Ghosal, D., Wienand, U., Peterson, P. A. and Saedler, H. (1987) The regulatory c1 locus of Zea mays encodes a protein with homology to myb proto-oncogene products and with structural similarities to transcriptional activators. *EMBO J.* 6, 3553–3558.

Qu, R., Wang, S.-M., Lin, Y.-H., Vance, V. B. and Huang, A. H. C. (1986) Characteristics and biosynthesis of membrane proteins of lipid bodies in the scuttela of maize. *Biochem J.* 235, 57–65.

Rohde, W., Dörr, S., Salamini, F. and Becker, B. (1991) Structure of a chalcone synthase gene from Hordeum vulgare. *Plant Mol. Biol.* 16, 1103–1106.

Roth, B. A., Goff, S. A., Klein, T. M. and Fromm, M. E. (1991) C1- and R-dependent expression of the maize Bz1 gene requires sequences with homologies to mammalian myb and myc binding sites. *Plant Cell* 3, 317–325.

Sambrook, L., Fritsch, E. F. and Maniatis, T. (1989) *Molecular Cloning, a Laboratory Manual*. New York: Cold Spring Harbor Laboratory Press.

Schmelzer, E., Jahnen, W. and Hahlbrock, K. (1988) In situ localization of light-induced chalcone synthetase mRNA, chalcone synthetase, and flavonoid end products in epidermal cells of parsley leaves. *Proc. Natl. Acad. Sci. U.S.A.* 85, 2989–2993.

Selden, R. F. (1987) Analysis of RNA by Northern Hybridization. In *Current Protocols in Molecular Biology* (Ausubel, F. M. et al., eds.). New York: Green Publishing Associates and Wiley-Interscience, pp. 4.9.1–4.9.8.

Shimamoto, K., Terada, R., Izawa, T. and Fujimoto, H. (1989) Fertile transgenic rice plants regenerated from transformed protoplasts. *Nature* 338, 274–276.

Skriver, K., Leah, R., Müller-Uri, F., Olsen, F.-L. and Mundy, J. (1992) Structure and expression.

Slakeski, N. and Fincher, G. B. (1992) Developmental regulation of (1-3,1-4)-b-glucanase gene expression in barley. *Plant Physiol.* 99, 1226–1231.

Smith, L. M., Handley, J., Li, Y., Martin, H., Donovan, L. and Bowles, D. J. (1992) Temporal and spatial regulation of a novel gene in barley embryos. *Plant Mol. Biol.* 20, 255–266.

Somssich, I. E., Schmelzer, E., Kawalleck, P. and Hahlbrock, K. (1988) Gene structure and in situ transcript localization of the pathogenesis-related protein 1 in parsley. *Mol. Gen. Genet.* 213, 93–98.

Sossountzov, L., Riuz-Avila, L., Vignois, F., Jolliot, A., Arondel, V., Tchang, F., Grosbois, M., Guerbette, F., Miginiac, E., Delsney, M., Puigdomenech, P. and Kader, J.-C. (1991) Spatial and temporal expression pattern of a maize lipid transfer protein gene. *Plant Cell* 3, 923–933.

Sterk, P., Booij, H., Schellekens, G. A., Van Kammen, A. and De Vries, S. C. (1991) Cell-specific expression of the carrot EP2 lipid transfer protein gene. *Plant Cell* 3, 907–921.

Terada, R. and Shimamoto, K. (1990) Expression of CaMV35S-GUS gene in transgenic rice plants. *Mol. Gen. Genet.* 220, 389–392.

Terada, R., Nakayama, T., Iwabuchi, M., Shimamoto, K. (1993) A wheat histone H3 promoter confers cell division-dependent and -independent expression of the GUSA gene in transgenic rice plants. *Plant J* 3: 241–252.

Tchang, F., This, P., Stiefel, V., Arondel, V., Morch, M. D., Pages, M., Puigdomenech, P., Grellet, F., Delsney, M., Bouillon, P., Huet, J. C., Guerbette, F., Beauvais-Cante, F., Duranton, H., Pernollet, J. C. and Kader, J.-C. (1988) Phospholipid transfer protein: Full-length cDNA and amino acid sequence in maize. *J. Biol. Chem.* 263, 16849–16855.

Thoma, S., Kaneko, Y. and Sommerville, C. (1993) A non-specific lipid transfer protein from Arabidopsis is a cell wall protein. *The Plant Journal* 3(3), 427–436.

von Heijne, G. (1988) Transcending the impenetrable: How proteins come to term with the membranes. *Biochim. Biophys. Acta.* 947, 307–333.

Watanabe, S. and Yamada, M. (1986) Purification and characterization of a nonspecific lipid transfer protein from germinated castor bean endosperms which transfers phospholipids and galactolipids. *Biochim. Biophys. Acta.* 876, 116–123.

Weston, K. (1992) Extension of the DNA binding consensus of the chicken c-Myb and v-Myb proteins. *Nucleic Acids Res.* 20, 3043–3049.

We claim:

1. A Ltp2 gene promoter comprising the sequence as shown in SEQ. I.D. 1, or a sequence variant or derivative thereof that when placed in a monocotyledonous plant demonstrates aleurone-tissue-specific expression when operably linked to a gene of interest.

2. The promoter of claim 1 wherein the promoter is a barley aleurone specific promoter.

3. The promoter of claim 2 wherein the promoter is for a 7 kDa lipid transfer protein.

4. The promoter of claim 1 wherein the promoter is the promoter for Ltp2 of Hordeum vulgare.

5. A gene construct comprising a gene of interest and a Ltp2 gene promoter comprising the sequence as shown in SEQ. I.D. 1, or a sequence variant thereof or derivative thereof that when placed in a monocotyledonous plant demonstrates aleurone-tissue-specific expression.

6. The construct of claim 5 wherein each of the myb site and the myc site in the Ltp2 gene promoter is maintained substantially intact.

7. The construct of claim 6 wherein the construct further comprises at least one additional sequence to increase expression of the GOI.

8. An in vivo expression system comprising a construct comprising a gene of interest and a Ltp2 gene promoter comprising the sequence as shown in SEQ. I.D. 1, or a sequence variant thereof or derivative thereof that when placed in a monocotyledonous plant demonstrates aleurone-tissue-specific expression.

9. The expression system of claim 8 wherein each of the myb site and the myc site in the Ltp2 gene promoter is maintained substantially intact.

10. The expression system of claim 9 wherein the monocotyledon is a cereal.

11. The expression system of claim 10 wherein the cereal is a developing cereal grain.

12. The expression system of claim 11 wherein the cereal seed is any one of a rice, maize, wheat, or barley seed, preferably maize.

13. The expression system of claim 8 wherein the construct further comprises at least one additional sequence to increase expression of the gene of interest.

14. An expression system according to claim 12 wherein the cereal seed is selected from the group consisting of rice and barley seed.

\* \* \* \* \*

SEQUENCE LISTING ( 1 ) GENERAL INFORMATION:

( i i i ) NUMBER OF SEQUENCES: 7

( 2 ) INFORMATION FOR SEQ ID NO:1:

( i ) SEQUENCE CHARACTERISTICS:
        ( A ) LENGTH: 807
        ( B ) TYPE: nucleic acid
        ( C ) STRANDEDNESS: single
        ( D ) TOPOLOGY: linear ( i i ) MOLECULE TYPE:
        ( A ) DESCRIPTION: DNA (genomic)

( v ) FRAGMENT TYPE: terminal fragment ( i x ) FEATURE:
        ( A ) NAME/KEY: Ltp2 gene promoter ( x i ) SEQUENCE DESCRIPTION: SEQ ID NO:1:

```
                     GATCTCG   ATGTGTAGTC   TACGAGAAGG     27
GTTAACCGTC   TCTTCGTGAG   AATAACCGTG   GCCTAAAAAT     67
AAGCCGATGA   GGATAAATAA   AATGTGGTGG   TACAGTACTT    107
CAAGAGGTTT   ACTCATCAAG   AGGATGCTTT   TCCGATGAGC    147
TCTAGTAGTA   CATCGGACCT   CACATACCTC   CATTGTGGTG    187
AAATATTTTG   TGCTCATTTA   GTGATGGGTA   AATTTTGTTT    227
ATGTCACTCT   AGGTTTTGAC   ATTTCAGTTT   TGCCACTCTT    267
AGGTTTTGAC   AAATAATTTC   CATTCCGCGG   CAAAAGCAAA    307
ACAATTTTAT   TTTACTTTTA   CCACTCTTAG   CTTTCACAAT    347
GTATCACAAA   TGCCACTCTA   GAAATTCTGT   TTATGCCACA    387
```

```
GAATGTGAAA    AAAAACACTC    ACTTATTTGA    AGCCAAGGTG    427
TTCATGGCAT    GGAAATGTGA    CATAAAGTAA    CGTTCGTGTA    467
TAAGAAAAAA    TTGTACTCCT    CGTAACAAGA    GACGGAAACA    507
TCATGAGACA    ATCGCGTTTG    GAAGGCTTTG    CATCACCTTT    547
GGATGATGCG    CATGAATGGA    GTCGTCTGCT    TGCTAGCCTT    587
CGCCTACCGC    CCACTGAGTC    CGGGCGGCAA    CTACCATCGG    627
CGAACGACCC    AGCTGACCTC    TACCGACCGG    ACTTGAATGC    667
GCTACCTTCG    TCAGCGACGA    TGGCCGCGTA    CGCTGGCGAC    707
GTGCCCCCGC    ATGCATGGCG    GCACATGGCG    AGCTCAGACC    747
GTGCGTGGCT    GGCTACAAAT    ACGTACCCCG    TGAGTGCCCT    787
AGCTAGAAAC    TTACACCTGC                                807
```

( 2 ) INFORMATION FOR SEQ ID NO:2:

( i ) SEQUENCE CHARACTERISTICS:
        ( A ) LENGTH: 846
        ( B ) TYPE: nucleic acid
        ( C ) STRANDEDNESS: single
        ( D ) TOPOLOGY: linear ( i i ) MOLECULE TYPE:
        ( A ) DESCRIPTION: DNA ( v ) FRAGMENT TYPE: terminal fragment ( i x ) FEATURE:
        ( A ) NAME/KEY: Ltp2 gene promoter and nucleotides for
            GUS fusion ( x i ) SEQUENCE DESCRIPTION: SEQ ID NO:2:

```
              GATCTCG    ATGTGTAGTC    TACGAGAAGG    27
GTTAACCGTC    TCTTCGTGAG    AATAACCGTG    GCCTAAAAAT    67
AAGCCGATGA    GGATAAATAA    AATGTGGTGG    TACAGTACTT    107
CAAGAGGTTT    ACTCATCAAG    AGGATGCTTT    TCCGATGAGC    147
TCTAGTAGTA    CATCGGACCT    CACATACCTC    CATTGTGGTG    187
AAATATTTTG    TGCTCATTTA    GTGATGGGTA    AATTTTGTTT    227
ATGTCACTCT    AGGTTTTGAC    ATTTCAGTTT    TGCCACTCTT    267
AGGTTTTGAC    AAATAATTTC    CATTCCGCGG    CAAAAGCAAA    307
ACAATTTTAT    TTTACTTTTA    CCACTCTTAG    CTTTCACAAT    347
GTATCACAAA    TGCCACTCTA    GAAATTCTGT    TTATGCCACA    387
GAATGTGAAA    AAAAACACTC    ACTTATTTGA    AGCCAAGGTG    427
TTCATGGCAT    GGAAATGTGA    CATAAAGTAA    CGTTCGTGTA    467
TAAGAAAAAA    TTGTACTCCT    CGTAACAAGA    GACGGAAACA    507
TCATGAGACA    ATCGCGTTTG    GAAGGCTTTG    CATCACCTTT    547
GGATGATGCG    CATGAATGGA    GTCGTCTGCT    TGCTAGCCTT    587
CGCCTACCGC    CCACTGAGTC    CGGGCGGCAA    CTACCATCGG    627
CGAACGACCC    AGCTGACCTC    TACCGACCGG    ACTTGAATGC    667
GCTACCTTCG    TCAGCGACGA    TGGCCGCGTA    CGCTGGCGAC    707
GTGCCCCCGC    ATGCATGGCG    GCACATGGCG    AGCTCAGACC    747
```

| | | | | |
|---|---|---|---|---|
| GTGCGTGGCT | GGCTACAAAT | ACGTACCCCG | TGAGTGCCCT | 787 |
| AGCTAGAAAC | TTACACCTGC | AACTGCGAGA | GCGAGCGTGT | 827 |
| GAGTGTAGCC | GAGTAGATC | | | 846 |

( 2 ) INFORMATION FOR SEQ ID NO:3:

( i ) SEQUENCE CHARACTERISTICS:
        ( A ) LENGTH: 1327
        ( B ) TYPE: nucleic acid
        ( C ) STRANDEDNESS: single
        ( D ) TOPOLOGY: linear ( i i ) MOLECULE TYPE:
        ( A ) DESCRIPTION: DNA ( v ) FRAGMENT TYPE: gene ( i x ) FEATURE:
        ( A ) NAME/KEY: Ltp2 gene ( x i ) SEQUENCE DESCRIPTION: SEQ ID NO:3:

| | | | | |
|---|---|---|---|---|
| | GATCTCG | ATGTGTAGTC | TACGAGAAGG | 27 |
| GTTAACCGTC | TCTTCGTGAG | AATAACCGTG | GCCTAAAAAT | 67 |
| AAGCCGATGA | GGATAAATAA | AATGTGGTGG | TACAGTACTT | 107 |
| CAAGAGGTTT | ACTCATCAAG | AGGATGCTTT | TCCGATGAGC | 147 |
| TCTAGTAGTA | CATCGGACCT | CACATACCTC | CATTGTGGTG | 187 |
| AAATATTTTG | TGCTCATTTA | GTGATGGGTA | AATTTTGTTT | 227 |
| ATGTCACTCT | AGGTTTTGAC | ATTTCAGTTT | TGCCACTCTT | 267 |
| AGGTTTTGAC | AAATAATTTC | CATTCCGCGG | CAAAAGCAAA | 307 |
| ACAATTTTAT | TTTACTTTTA | CCACTCTTAG | CTTTCACAAT | 347 |
| GTATCACAAA | TGCCACTCTA | GAAATTCTGT | TTATGCCACA | 387 |
| GAATGTGAAA | AAAAACACTC | ACTTATTTGA | AGCCAAGGTG | 427 |
| TTCATGGCAT | GGAAATGTGA | CATAAAGTAA | CGTTCGTGTA | 467 |
| TAAGAAAAAA | TTGTACTCCT | CGTAACAAGA | GACGGAAACA | 507 |
| TCATGAGACA | ATCGCGTTTG | GAAGGCTTTG | CATCACCTTT | 547 |
| GGATGATGCG | CATGAATGGA | GTCGTCTGCT | TGCTAGCCTT | 587 |
| CGCCTACCGC | CCACTGAGTC | CGGGCGGCAA | CTACCATCGG | 627 |
| CGAACGACCC | AGCTGACCTC | TACCGACCGG | ACTTGAATGC | 667 |
| GCTACCTTCG | TCAGCGACGA | TGGCCGCGTA | CGCTGGCGAC | 707 |
| GTGCCCCCGC | ATGCATGGCG | GCACATGGCG | AGCTCAGACC | 747 |
| GTGCGTGGCT | GGCTACAAAT | ACGTACCCCG | TGAGTGCCCT | 787 |
| AGCTAGAAAC | TTACACCTGC | AACTGCGAGA | GCGAGCGTGT | 827 |
| GAGTGTAGCC | GAGTAGATCA | CCGTACGACG | ACGACGAGGG | 867 |
| GCATGGCGAT | GGCGATGGGG | ATGGCGATGA | GGAAGGAGGC | 907 |
| AGCGGTGGCC | GTGATGATGG | TGATGGTGGT | GACGCTGGCG | 947 |
| GCGGGTGCGG | ACGCGGGAGC | GGGAGCGGCG | TGCGAGCCGG | 987 |
| CGCAGCTGGC | GGTGTGCGCG | TCGGCGATCC | TGGGCGGGAC | 1027 |
| GAAGCCGAGC | GGCGAGTGCT | GCGGGAACCT | GCGGGCGCAG | 1067 |
| CAGGGGTGCT | TGTGCCAGTA | CGTCAAGGAC | CCCAACTACG | 1107 |

| | | | | |
|---|---|---|---|---|
| GGCACTACGT | GAGCAGCCCA | CACGCGCGCG | ACACCCTCAA | 1147 |
| CTTGTGCGGC | ATACCCGTAC | CGCACTGCTA | GCCGCCTAGC | 1187 |
| CGATCGAGGG | CTCCAGGCAC | GCATGCATGT | TCCTGTTATG | 1227 |
| TGTATGTTGG | AATAAAATGC | TGGTGATCTA | TGGCGGCTAG | 1267 |
| CTTGCTTCCT | GGCTAGCAGC | TGCTGTAATG | AAATTTGTGT | 1307 |
| TGCAACTTTT | TTTTTAGTCC | | | 1327 |

( 2 ) INFORMATION FOR SEQ ID NO:4:

( i ) SEQUENCE CHARACTERISTICS:
        ( A ) LENGTH: 17
        ( B ) TYPE: nucleic acid
        ( C ) STRANDEDNESS: single
        ( D ) TOPOLOGY: linear ( i i ) MOLECULE TYPE:
        ( A ) DESCRIPTION: oligonucleotide ( v ) FRAGMENT TYPE: synthetic DNA ( i x ) FEATURE:
        ( D ) OTHER INFORMATION: KS primer used in preparing constructs ( x i ) SEQUENCE DESCRIPTION: SEQ ID NO:4:

CGAGGTCGAC    GGTATCG    17

( 2 ) INFORMATION FOR SEQ ID NO:5:

( i ) SEQUENCE CHARACTERISTICS:
        ( A ) LENGTH: 20
        ( B ) TYPE: nucleic acid
        ( C ) STRANDEDNESS: single
        ( D ) TOPOLOGY: linear ( i i ) MOLECULE TYPE:
        ( A ) DESCRIPTION: oligonucleotide ( v ) FRAGMENT TYPE: synthetic DNA ( i x ) FEATURE:
        ( D ) OTHER INFORMATION: PLT11 primer used in preparing constructs ( x i ) SEQUENCE DESCRIPTION: SEQ ID NO:5:

TACGGTGATC    TACTCGGCTA    20

( 2 ) INFORMATION FOR SEQ ID NO:6:

( i ) SEQUENCE CHARACTERISTICS:
        ( A ) LENGTH: 19
        ( B ) TYPE: nucleic acid
        ( C ) STRANDEDNESS: single
        ( D ) TOPOLOGY: linear ( i i ) MOLECULE TYPE:
        ( A ) DESCRIPTION: oligonucleotide ( v ) FRAGMENT TYPE: synthetic DNA ( i x ) FEATURE:
        ( D ) OTHER INFORMATION: LTP13 primer used in preparing constructs ( x i ) SEQUENCE DESCRIPTION: SEQ ID NO:6:

ACGAAGCCGA    GCGGCGAGT    19

( 2 ) INFORMATION FOR SEQ ID NO:7:

( i ) SEQUENCE CHARACTERISTICS:
        ( A ) LENGTH: 31
        ( B ) TYPE: nucleic acid
        ( C ) STRANDEDNESS: single
        ( D ) TOPOLOGY: linear ( i i ) MOLECULE TYPE:
        ( A ) DESCRIPTION: oligonucleotide ( v ) FRAGMENT TYPE: synthetic DNA ( i x ) FEATURE:
        ( D ) OTHER INFORMATION: PLT15 primer used in preparing constructs ( x i ) SEQUENCE DESCRIPTION: SEQ ID NO:7:

```
GGACTAAAAA    AAAAGTTGCA    ACACAAATTT    C            31
```